US006200820B1

United States Patent
Hansen et al.

(10) Patent No.: US 6,200,820 B1
(45) Date of Patent: *Mar. 13, 2001

(54) LIGHT SCATTER-BASED IMMUNOASSAY

(75) Inventors: W. Peter Hansen, Cambridge, MA (US); Michael Cennerazzo, Weehauken, NJ (US); Carl Theodore Edens; Manish Kochar, both of Columbia, MD (US)

(73) Assignee: Sienna Biotech, Inc., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/473,187

(22) Filed: Jun. 7, 1995

Related U.S. Application Data

(63) Continuation-in-part of application No. 08/286,778, filed on Aug. 5, 1994, now Pat. No. 5,589,401, which is a continuation of application No. 07/994,903, filed on Dec. 22, 1992, now abandoned.

(51) Int. Cl.$^7$ .................. G01N 33/543; G01N 33/546; G01N 33/552; G01N 33/553

(52) U.S. Cl. .................. 436/523; 435/7.1; 435/6; 436/501; 436/518; 436/525; 436/527; 436/534; 436/164

(58) Field of Search .................. 436/501, 518, 436/523, 525, 533, 164, 527, 534; 435/7.1, 6, 7.93, 7.94

(56) References Cited

U.S. PATENT DOCUMENTS

| | | |
|---|---|---|
| 3,873,204 | 3/1975 | Friedman et al. . |
| 4,305,925 | 12/1981 | Kapmeyer et al. . |
| 4,313,734 | 2/1982 | Leuvering . |
| 4,446,239 | 5/1984 | Tsuji et al. . |
| 4,480,042 | 10/1984 | Craig et al. . |
| 4,581,334 | 4/1986 | Kirchanski . |
| 4,853,335 | 8/1989 | Olsen et al. . |
| 5,017,009 | 5/1991 | Schutt et al. . |
| 5,079,172 | 1/1992 | Hari et al. . |
| 5,162,863 | 11/1992 | Ito . |
| 5,286,452 * | 2/1994 | Hansen et al. .................. 422/73 |
| 5,369,037 * | 11/1994 | Hansen .................. 436/533 |
| 5,585,241 * | 12/1996 | Lindmo .................. 436/523 |
| 5,589,401 * | 12/1996 | Hansen et al. .................. 436/525 |

FOREIGN PATENT DOCUMENTS

| | | |
|---|---|---|
| 0258963 | 9/1988 | (EP) . |
| 0287665 | 10/1988 | (EP) . |
| 0426300 | 9/1990 | (EP) . |
| 8906801 | 7/1989 | (WO) . |
| 89/11101 * | 11/1989 | (WO) . |

OTHER PUBLICATIONS

McHugh et al., "Flow Cytometric Detection & Quantitation of Immune Complexes Using $CL_q$–Coated Microspheres," *Journal of Immunological Methods*, vol. 95, 1986, pp. 57–61.*
Bohmer et al., "Flow Cytometric Analysis of Immunogold Cell Surface Label," *Cytometry*, vol. 5, 1984, pp. 543–546.*
Gribnau et al., "Particle–Labelled Immunoassays: a Review", *Journal of Chromatography*, vol. 376, 1986, pp. 175–189.*
H. Bauer, et al. Experientia, 31:1149–1151 (1975).
M. Horisberger, et al., J. of Histochem. and Cytochem., 25(No. 4):295–305 (1977).
M. Horisberger, Biol. Cellularie, 36:253–258 (1979).
J.H.W. Leuvering, et al., J. of Immunological Methods, 62:163–74 (1983).
J.H.W. Leuvering, et al., J. of Immunological Methods, 45:183–94 (1981).
F. Wielaard, et al., J. of Virological Methods, 17:149–158 (1987).
Duke Scientific Corporation Bulletin 88C Sep. 1,1990, "Covaspheres Reagents".
Duke Scientific Corporation Bulletin 93D Apr. 1, 1992 "Fluorescent Microspheres & Particles".
Horisberger, et al., Experientia, 31:1147–9 (1975).
Rohr, et al., Analytical Biochemistry, 182:388–398 (1989).
Saunders, G.C. et al., Clinical Chemistry 31(12):2020–2023 (1985).
Van Erp, et al. , J. Immunoassay, 12:425–443 (1991).
Odell, et al., Principles of Competitive Protein–Binding Assays, ed. 13:243–254 (1983).
Sakai, et al., Chem. Pharm. Bull. 37(11):3010–14 (1989).

* cited by examiner

*Primary Examiner*—Long V. Le
*Assistant Examiner*—James L. Grun
(74) *Attorney, Agent, or Firm*—Lerner, David, Littenberg, Krumholz & Mentlik, LLP

(57) ABSTRACT

Disclosed are an optical flow particle apparatus and method for conducting a particle light scatter-based immunoassay for simultaneously measuring the presence or amount of one or more analytes in a fluid sample which involves the use of a reagent set for each analyte including first binding molecule-coated monodisperse microspheres and second binding molecule-coated colloidal particles in which at least one of the first or second binding molecules specifically binds a respective one of the analytes. In the case where more than one analytes are detected, each monodisperse microperse microsphere of a particular reagent set has a light scatter signal resolvable from that of microspheres of any other reagent set. Changes determined in the distributions of the measured light scatter signals for individual microspheres of each of the particular reagent sets are indicative of the presence or amount of the respective analyte(s) in the sample.

57 Claims, 12 Drawing Sheets

POLYSTYRENE SPHERE (MONONISPERSED IN SIZE) APPROX 1 MICRON DIAMETER

● COLLOIDAL METAL PARTICLE (POLYDISPERSED IN SIZE APPROX 20 nm TO 120nm DIAMETER)

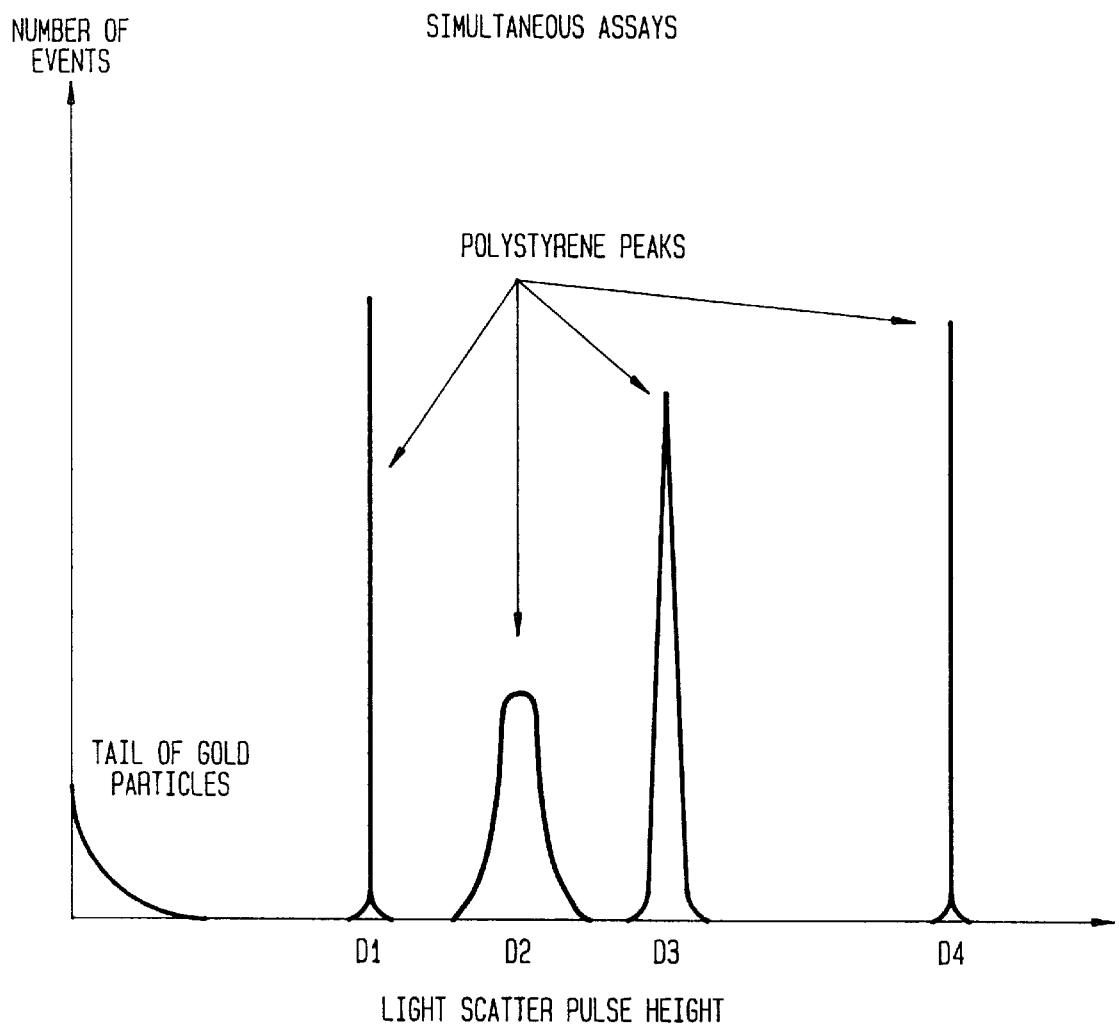

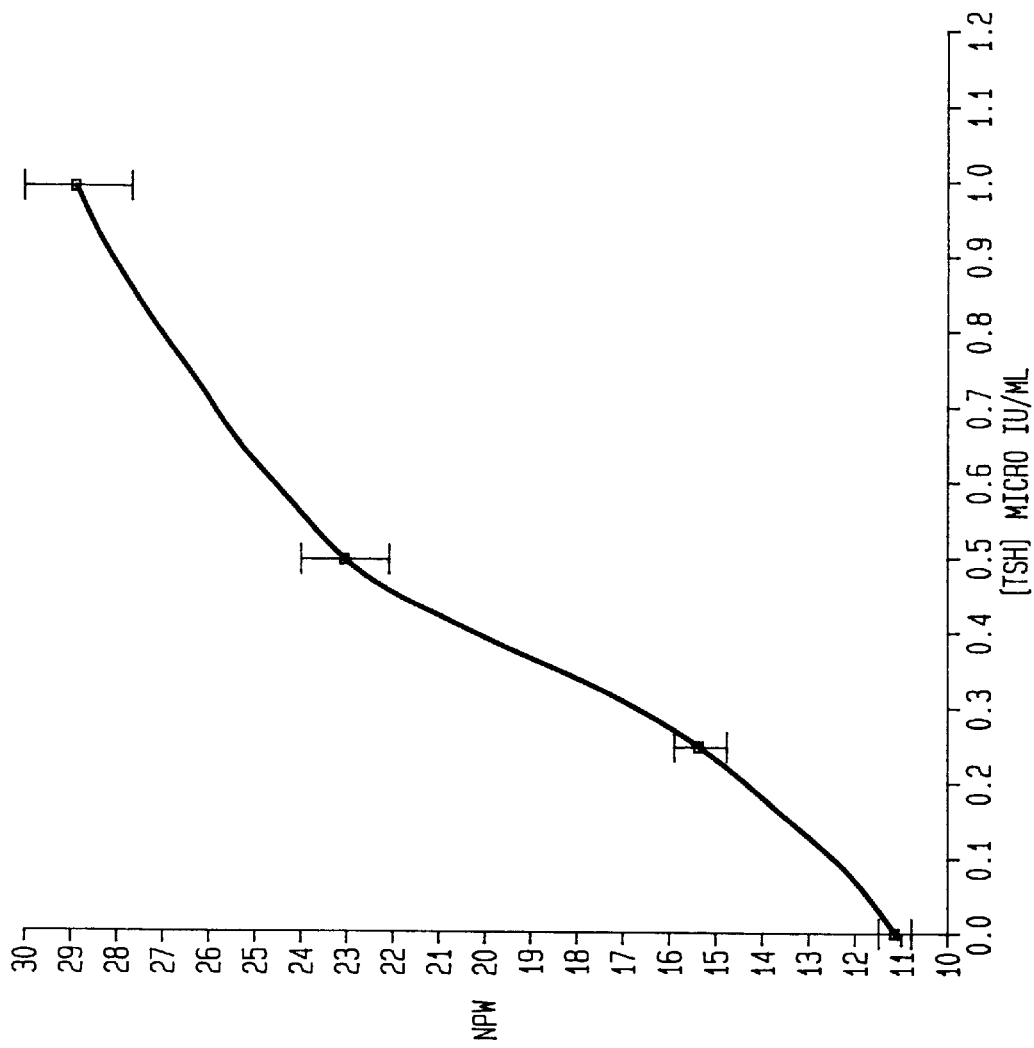

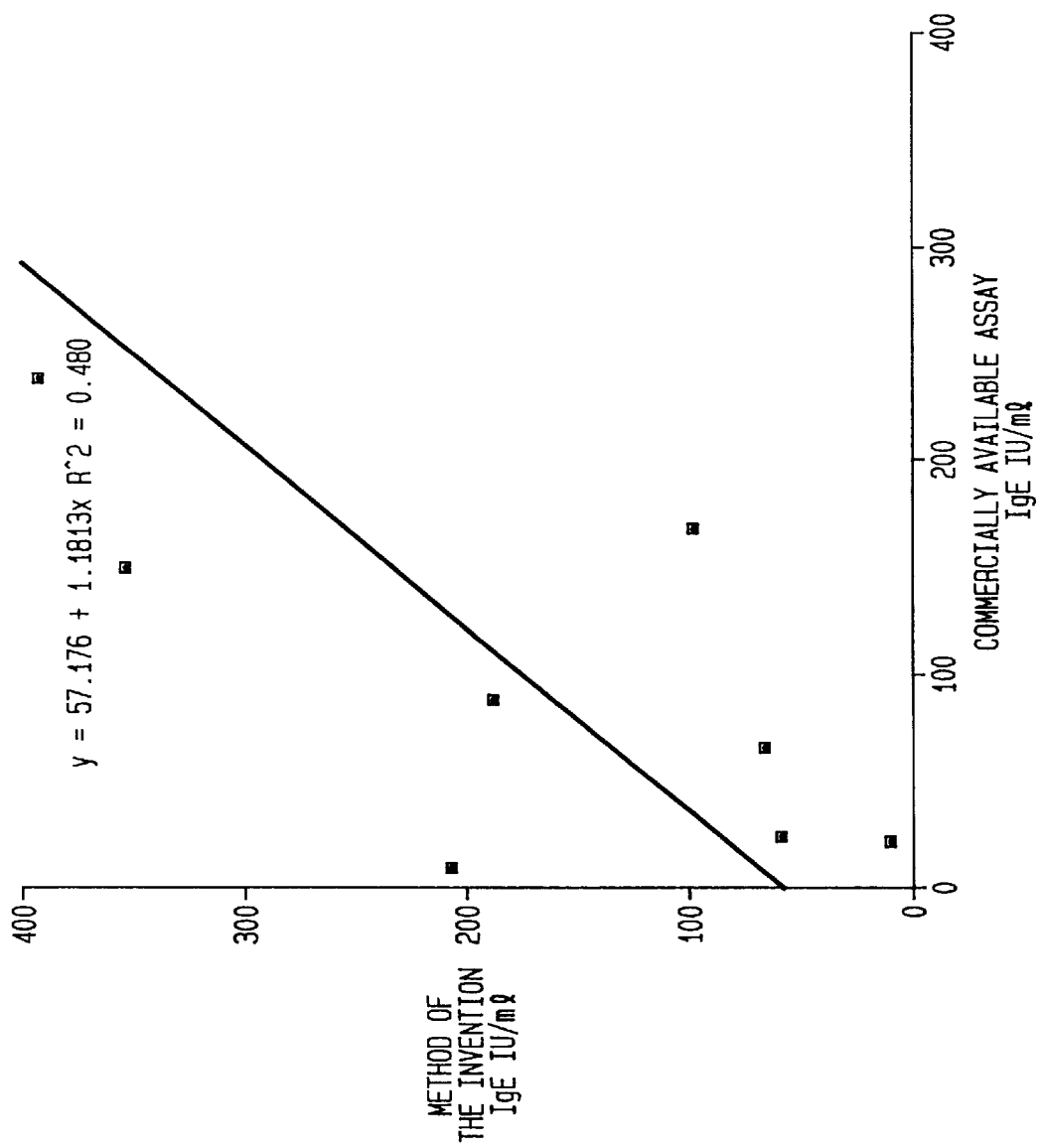

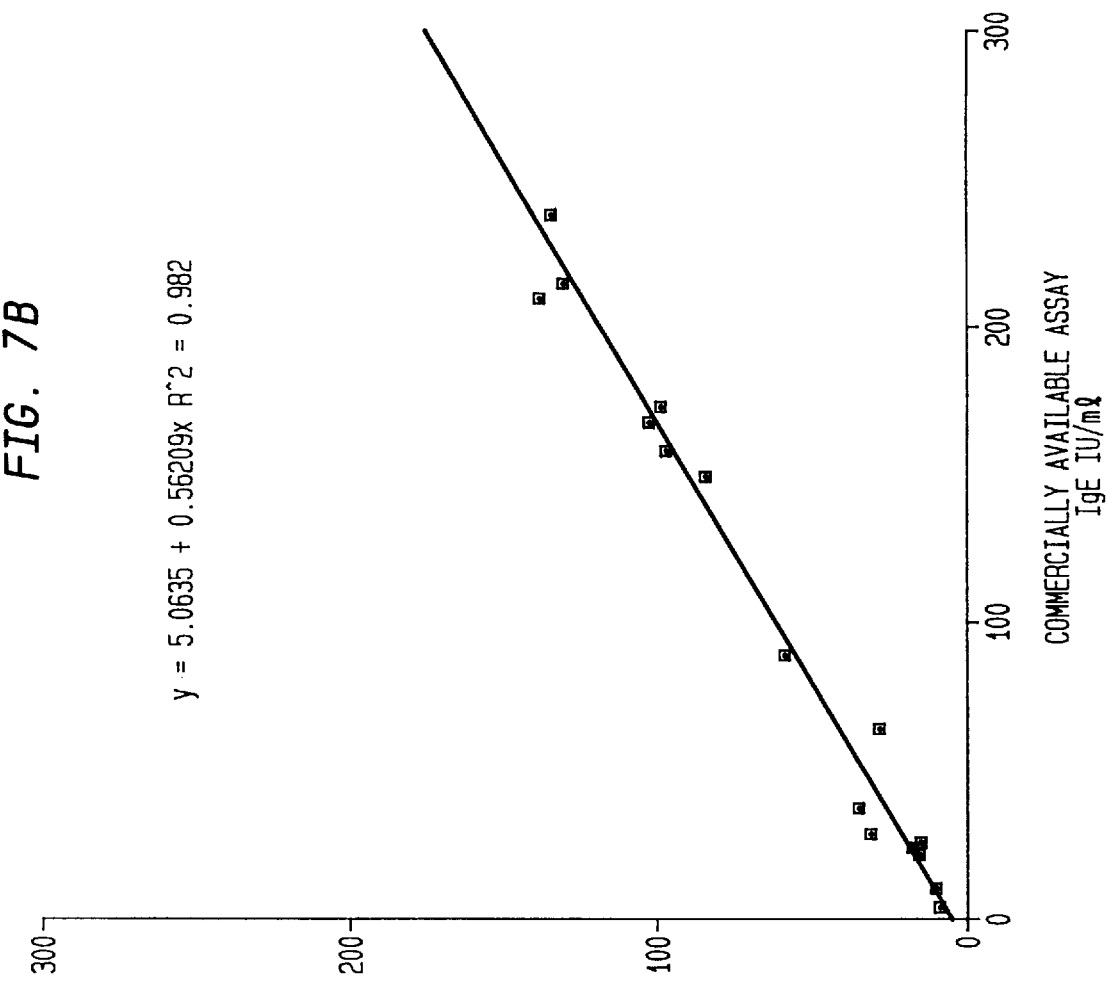

LIGHT SCATTER-BASED IMMUNOASSAY

CROSS-REFERENCE TO RELATED APPLICATIONS

This is a continuation-in-part of U.S. patent application Ser. No. 08/286,778, filed Aug. 5, 1994 now U.S. Pat. No. 5,589,401, which is a continuation of U.S. patent application, Ser. No. 07/994,903, filed Dec. 22, 1992, abandoned, the contents of which are hereby incorporated by reference in their entireties.

BACKGROUND OF THE INVENTION

1. Field of the Invention

The invention relates broadly to immunoassay methods for measuring one or more analytes in a fluid sample by measuring light scatter signals from particles in a flow particle analyzer. More particularly, the invention relates to measuring changes in light scatter signals from monodisperse microspheres as the result of analyte-mediated binding to such microspheres of colloidal particles.

2. Description of the Prior Art

Antibodies, antigens and many haptens exhibit high affinities, not only for their complementary proteins, but also for certain solid surfaces such as those found in the wells of plastic microtiter plates, walls of plastic test tubes, polymeric microspheres, and colloidal metal particles. Exploitation of these properties has led to a revolution in the field of diagnostic assay methods for the aforementioned analytes in fluid samples such as serum.

The ability to carry out antigen-antibody interactions on solid supports has greatly simplified the separation of analyte-containing immunocomplexes from unused reactants and interfering substances, such as those often present in biological fluids. Such systems are generally referred to as "solid phase immunoassays" or "immunosorbent assays", and fall within the genus of "heterogeneous immunoassays." While the phase separation steps in heterogeneous immunoassays are valuable in reducing interferences by nonspecific binding substances that generally have an adverse effect on the sensitivity of the assay method, such assays are cumbersome and expensive, and are a focal point for reliability problems in automated systems.

Additionally, such heterogeneous systems have the additional disadvantage of requiring that one or another member of the immunocomplex be labeled with a molecule that can be easily quantified. Such molecules are generally referred to as "reporter molecules" and include radioisotopes (radioimmunoassays, RIA), enzymes (enzyme-linked immunoassays generally coupled with a chromophore, ELISA), fluorescent molecules (fluorescence immunoassays, FIA), chemiluminescent molecules (CIA), gold particles, photosensitive molecules, and the like. For a review, see Kemeny, D. M., et al., Immunology Today 7, 67 (1986). Further, because of the limited number of chromophores and fluorophores available as reporter molecules, and the extensive overlap of emission spectra of such molecules, simultaneous assay of multiple analytes are not suitable using these reporters. For example, Cambridge Biotech's simultaneous EIA assays for HIV-1 and HIV-2 are not separable.

"Homogeneous immunoassay" is the term applied to immunoassays in which no phase separation occurs. Such systems, which include binding protein-coated particle agglutination assays, are useful because they have fewer steps to automate, and automation is mechanically, fluidically and electrically simple. Examples of immunoassays requiring no phase separation steps include: latex microsphere agglutination, hemagglutination, and fluorescence depolarization assays. Examples of latex bead agglutination assays for single analytes are found in U.S. Pat. Nos. 4,521,521; 4,184,849; 4,279,617; 4,191,739; and 4,851,329, and for multiple analytes in a single fluid sample in Hansen, copending U.S. patent application Ser. No. 07/883,574, now U.S. Pat. No. 5,286,452. Nephelometric or turbidimetric automated systems for agglutination or fluorescence depolarization assays are simple, inexpensive to construct, and, unlike heterogeneous assays, do not require frequent maintenance of the complicated phase separation apparatus.

The presence of interfering substances in body fluids however, has inhibited otherwise promising homogeneous immunoassay approaches from meeting the high sensitivity requirements of many medically important tests, such as aremet by ELISA and RIA. For reviews of this problem see, for example, Masson et al., *Methods in Enzymology*, 74:115 (1981) and Collett-Cassart et al., *Clin Chem.*, 27:64 (1981). By contrast, methods according to preferred embodiments of the present invention provide immunoassays that can be free from non-specific interferences, at least to a sensitivity level of about $5\times10^{-13}$ M. This level of sensitivity is two to three orders of magnitude greater than prior art homogeneous; latex bead agglutination assays. See, e.g., alpha-fetoprotein ($3\times10^{-10}$ M, Collett-Cassart et al., above), urinary HCG ($6\times10^{-11}$ M, Lentrichia et al., *J. Immunol Meth.*, 89:657 (1986) (but exhibiting only an 87% correlation with RIA at analyte levels 20 times the claimed sensitivity limit), and serum digoxin by a fluorescence depolarization method ($3\times10^{-10}$ M, S. Wong in D. Chan, ed., *Immunoassay Automation*, Academic Press, 1992, p. 329).

Prior art approaches to eliminating or decreasing the undesirable effects of non-specific interfering substance on homogeneous immunoassays have been generally unsatisfactory. These include: high dilution of body fluid sample (Fritz et al., *J. Immunol.*, 108:110(1972), but this proportionally decreases sensitivity; using antibody fragments (Masson, Id.), but this approach is expensive and unpredictable; and, use of special conditions of pH, ionic strength, and buffer type, and/or addition of chelators or other scavengers (Masson, Id.), but these introduce multiple dependent factors that must be optimized for each analyte, and can become prohibitively expensive and cumbersome (Lim et al., *J. Clin. Chem. Clin. Biochem.*, 20:141(1982).

Other approaches to solving the non-specific interference problem have included using IgG-coated latex ultramicrospheres to inhibit non-specific reactions in a latex sphere agglutination assay that uses antibody fragments. The sensitivity of one such agglutination method using a Coulter principle electronic resistance flow particle analyzer with a 30 μm orifice was reported to be about $5\times10^{-13}$ to $4\times10^{-12}$ M. Sakai et al., *Chem. Pharm. Bull.*, 37:3010 (1989). The disadvantages of this approach is that the additional reagent (non-specific, IgG coated ultramicrospheres) has an incremental manufacturing, quality control and storage cost associated with it. Preferred methods according to the present invention remove this important disadvantage by combining the action of specific immunoreactivity with an action that can improve specificity, all in one reagent. In addition, although the Coulteic principle particle counter used by Sakai et al. yields quantitative results, the need for the small (30 μm) orifice in order to sense agglutination has the problem of clogging during agglutination reactions (Masson, Id.). Certain methods according to the present invention can use a sheath flow particle analyzer with a large orifice, which eliminates clogging. However, in the Sakai et al. approach, the frequency distribution of the amplitude of the detected signals from light scattering of specifically agglutinated particles (dimers, trimers, etc) presents a problem in Coulter volume overlap if simultaneous assays of more than one analyte are attempted, a problem not encountered in the present invention as multimers generally are not formed and multiple simultaneous assays can be performed without complex: signal processing algorithms to remove the problem of detection signal overlap.

Another problem encountered in prior art agglutination immunoassays is the need for agitation by mechanical mixers during the entire reaction period of reaction mixtures containing particles of one micron or greater (Masson, Id.). A further advantage of the preferred methods according to the present invention, insofar as automation is concerned, is that agitation of samples is not needed to complete the reaction during useful time frames.

Schutt et al., EP 0254430 and U.S. Pat. No. 5,017,009, show a scattered total internal reflectance (STIR) assay method for an analyte in which colloidal gold particles are used as a label for proteins that bind to a coated macroscopic plastic plate of optical quality. This immunoassay relies upon the detection of back scattered light from an evanescent wave disturbed by the presence of a colloidal gold label brought to the interface by an immunological reaction. This evanescent wave is said to be the result of a totally internally reflected incident light wave. A disadvantage of this system is that the expensive optical-quality plastic plate is not reusable and must be discarded after a single use.

There remains an important need for an immunoassay method for antigens, antibodies, and haptens in fluid samples that combines the mechanical simplicity and low cost of particle agglutination homogeneous assays with the reduction in deleterious effects of interfering substances enjoyed by solid support based heterogeneous assays, and that does so with increased efficiency and scope when compared to prior art agglutination assays. This need is now fulfilled by the invention described in detail below.

SUMMARY OF THE INVENTION

One aspect of the present invention is directed to a particle light scatter-based immunoassay for measuring an analyte in a fluid sample, comprising the steps of:

a) combining with said fluid sample, first binding molecule-coated monodisperse microspheres having a resolvable light scatter signal and second binding molecule-coated colloidal particles, or a prior-prepared immunocomplex comprising said monodisperse microspheres, said analyte and said colloidal particles, to form a mixture and to allow a reaction to occur, said reaction being the formation or the decomplexation of the immunocomplex, respectively, so that the thus-reacted mixture includes relative amounts of non-colloidal particles selected from the group consisting of said immunocomplex and uncomplexed microspheres, the relative amounts of said immunocomplex and said uncomplexed microspheres being dependent upon the presence or amount of analyte in said fluid sample;

b) illuminating the non-colloidal particles with an incident light source to produce individual light scatter signals for each of the non-colloidal particles; and c) determining a statistical distribution of the thus-produced light scatter signals so that the distribution can be correlated with the presence or amount of said analyte in said fluid sample.

As further discussed below, this aspect of the invention incorporates the realization that the light scatter signals from complexed microspheres differ from those of uncompleted microspheres. In many cases, it is impossible to discriminate between the signal from an individual complexed microsphere and the signal from an individual uncomplexed microsphere. It has now been found, however, that the statistical distribution of individual light scatter signals from a large number of complexed microspheres differs from the statistical distribution of individual light scatter signals from a similar number of uncompleted microspheres, regardless of whether such individual signals can be distinguished. For example, the scatter signals from complexed and uncompleted microspheres typically exhibit close to the same mean amplitude. However, the peak amplitudes of light scatter signals from the complexed microspheres are more broadly scattered about the mean. Thus, if these peak amplitudes were plotted on a histogram or graph as the number of signals versus peak amplitude, each histogram would peak at close to the same mean peak amplitude. However, the histogram peak for the complexed microspheres would be broader, and would include more values relatively far from the mean.

In certain embodiments, the light scatter signal is generated from substantially low angle forward light scatter and/or substantially right angle light scatter, a histogram of the statistical distribution of the signals is produced, and normalized peak width of the histogram, i.e., the peak width at one-half peak height (NPW), is measured relative to a control parameter. In other embodiments, changes in the statistical distribution of other properties of the electrical signals resulting from detection of light scatter signals such as pulse amplitude, the product of pulse amplitude and pulse width, or integrated pulse area is determined.

Preferred immunoassays include forward binding reactions (sandwich assays), displacement assays, competition assays, and inhibition assays. In a preferred embodiment of a forward binding reaction, an immunocomplex is formed between large monodisperse polymeric microspheres coated with a first binding molecule, small colloidal particles coated with a second binding molecule, and an analyte that is complementary to both binding molecules. The statistical distribution of light scatter signals, such as a pulse height distribution histogram of the particulate immunocomplex, are compared with a control distribution of histogram dimensions (obtained with monodisperse coated polymeric microspheres in the absence of colloidal particles and/or linking analyte tested before, after, or during the analytical run). The change in the statistical distribution, such as in the histogram dimension, due to the presence of the analyte are correlated with the concentration of the analyte in the fluid sample.

In a preferred displacement embodiment of the invention, an immunocomplex reagent is first formed between monodisperse polymeric microspheres coated with the analyte and colloidal particles coated with an anti-analyte antibody; the light scatter signal histogram dimensions of the immunocomplex are determined before and after its exposure to the analyte; and the statistical changes of the histogram dimension after exposure to the analyte are correlated with analyte concentration in the fluid sample.

In a preferred competition embodiment of the invention, an analyte competes against anti-analyte antibody-coated colloidal particles for binding to monodisperse polymeric microspheres coated with a first binding molecule complementary to the anti-analyte antibody. A reduction in the extent of immunocomplex formation between the microspheres and colloidal particles caused by the analytic reduces a dimension of the light scatter signal pulse height distribution histograms in proportion to the concentration of analyte in the fluid sample.

In a preferred inhibition reaction embodiment, the immunoassay relies upon the ability of analyte to inhibit the binding of anti-analyte-coated colloidal particles to binding molecule-coated monodisperse polymeric microspheres.

The foregoing principles can be applied to monitor two or more analytes simultaneously. Thus, a further aspect of the present invention provides a particle light scatter-based immunoassay for simultaneously measuring two or more analytes in a single fluid sample, comprising the steps of:

(a) combining with the fluid sample for each of the first and second analytes, first binding molecule-coated monodisperse microspheres having a resolvable light scatter signal and second binding molecule-coated colloidal particles, or a prior-prepared immunocomplex comprising the monodisperse microspheres, the analyte and the colloidal particles to form a mixture and to allow a reaction to occur, the reaction being the formation or the decomplexation of the first and second immunocomplexes, respectively, so that the thus-reacted mixture includes relative amounts of non-colloidal particles selected from the group consisting of first and second immunocomplexes and first and second uncomplexed microspheres, the relative amounts of the first immunocomplex and the first uncomplexed microspheres, and the relative amounts of the second immunocomplex and the second uncomplexed microspheres being dependent upon the presence or amounts of the first and second analytes, respectively, in the fluid sample;

(b) illuminating the non-colloidal particles with an incident light source to produce individual light scatter signals for each of the non-colloidal particles; and (c) determining a statistical distribution of the thus-produced light scatter signals so that the distributions can be correlated with the presence or amount of the first and second analytes, respectively, in the fluid sample.

In another aspect of the present invention, excess colloidal particles relative to the monodisperse microspheres also act as scavengers that remove interfering non-specific substances present in the various immunoassay reaction mixtures.

A further aspect of the present invention provides improved apparatus for measuring the light scattering characteristics of particles. Apparatus according to this aspect of the invention includes:

(a) a flow cell defining a bore;

(b) means for passing a stream of liquid bearing the particles along the bore;

(c) means for directing light through the flow cell along a beam path transverse to the bore so that the light impinges on particles in the stream; and (d) detector means for detecting light scattered by the particles and providing signals representing strength of the detected light. In a preferred embodiment, the apparatus also includes sheath flow means for passing a stream of sheath liquid along the bore, wherein the sample liquid bearing the particles is contained within the stream of sheath liquid. The apparatus may further include cell and beam position feedback control means which automatically adjusts the relative positions of the flow cell and the beam path in response to signals from the detector so as to maximize the strength of the detected light as represented in the light scatter signals. In other preferred embodiments, the apparatus includes a dispersion sensing means which is, actuated when the sample fluid includes particles of known dispersive properties, which in turn actuates either the sample fluid source to reduce sample flow, or the sheath liquid fluid sources to increase sheath liquid flow, and to narrow sample stream.

These and other objects will become apparent by reference to the following detailed description of the preferred embodiments and the appended claims.

DESCRIPTION OF THE DRAWINGS

FIG. 2D illustrates at light scatter pulse height histogram for a simultaneous multiple-analyte assay.

FIG. 5A shows a human serum TSH assay standard curve;

FIGS. 7A and 7B show latex-latex agglutination assay correlation curves for IgE.

DETAILED DESCRIPTION OF THE PREFERRED EMBODIMENTS

Figure 1:
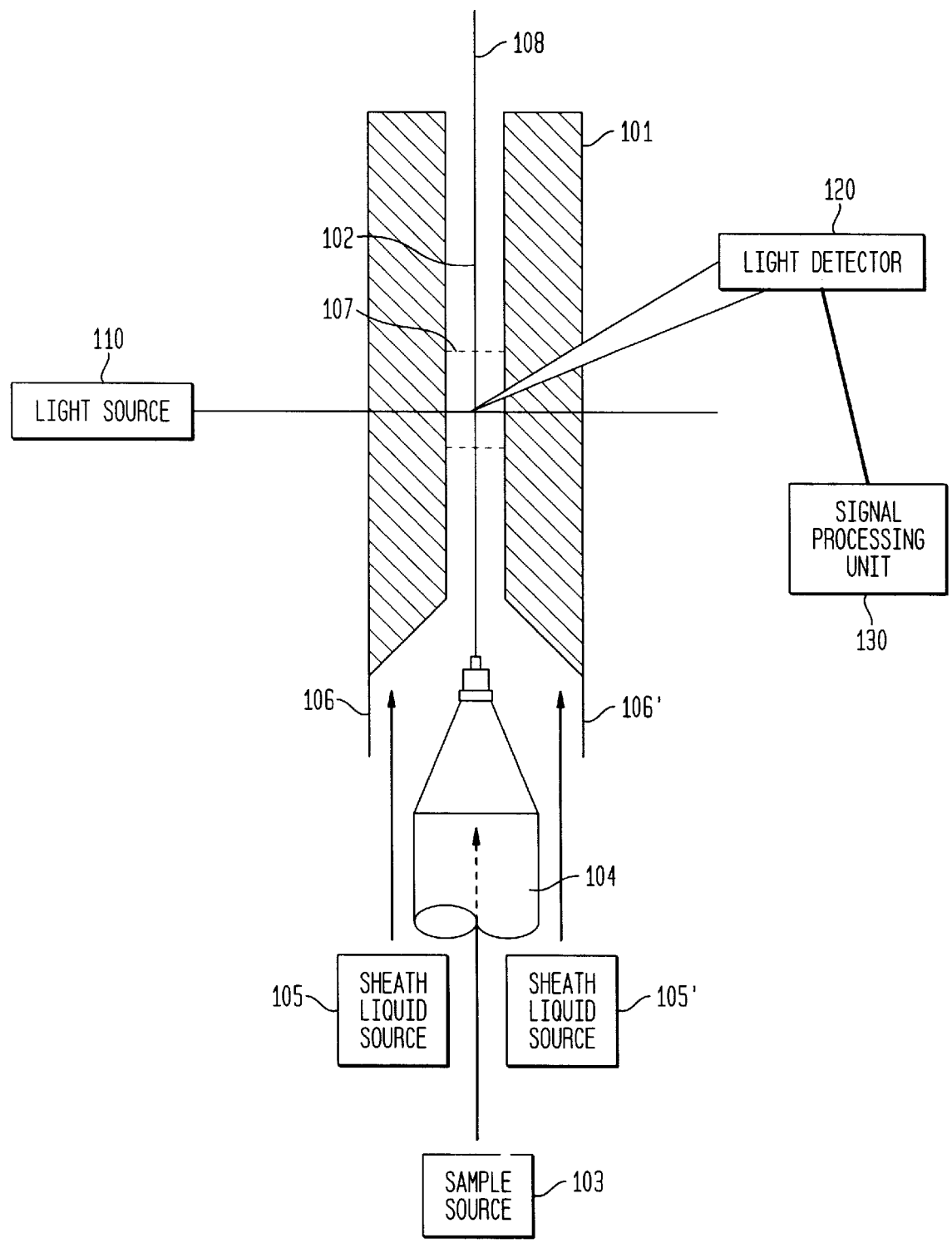
FIG. 1 illustrates a sectional view of apparatus for analyzing the light scatter properties of particles.

FIG. 1 illustrates an optical flow particle analyzer (FPA) wherein flow cell 101 defines a central bore 102. At one end of the f low cell, sample source 103 is in fluid connection with the larger end of funnel-shaped sample entrance port 104. Sheath liquid sources 105 and 105' located at the same end of the flow cell as port 104 are each in fluid connection with sheath liquid entrance ports 106 and 106', respectively. The sample liquid, which contains the particles to be analyzed, enters the flow cell through the sample entrance port, and the sheath liquid enters from entrance ports 106 and 106', each in a predetermined flow rate and flow volume. These flows cause the stream of particle-bearing liquid to be narrowed down at the end of the entrance port into a very narrow stream 108 having a maximum dimension of the same order of magnitude as the maximum dimension of the particles being carried by the stream. This dimension typically is in the order of 25 microns or smaller, e.g., from about 1 to about 10 microns. The sheath liquid provides a smooth and non-turbulent concentric flow around the particle stream. Sheath flow is known to obtain the maximum resolution in the light scatter signal of particle and particle aggregates because it constricts the stream of particle-bearing liquid to a narrow cross-section, and centers the particle stream in the highest intensity and most uniform region of the focused light beam.

Incident light source 110 emits a beam of incident light. The light source may include, e.g., a laser such as a helium-neon laser or a laser diode. The diameter of the beam of light emitted from the laser may be modified by a combination of lenses, mirrors, and other conventional optical elements incorporated in the light source. These elements may collimate and narrow the beam. The light source directs the incident light substantially perpendicular to bore 102, so that the incident light impinges upon the particle stream 108 at a substantially right angle, and scattered light is produced. The particle-scattered light exiting from the flow cell via viewing zone 107 is made to impinge on light detector 120. Such impingement may be achieved by a collection lens with a central beam blocker (not shown). Suitable light detectors include photodiodes, photomultipliers, phototransistors and photoresistors. Light scatter signals from the light detector are then analyzed by signal processing unit 130 which is connected to the light detector. Signal processing units may be hardware-based or software-based, and may include amplifiers, logic circuitry, digital counters, and electronic display devices. The following U.S. patents describe elements of sheath flow particle analyzers: U.S. Pat. Nos. 3,873,204, 3,785,735, and 3,705,771. The disclosures of these patents are namely incorporated by reference herein.

Methods according to one aspect of the invention take advantage of the discovery that statistical changes occur in measured values of certain physical properties of a preparation of relatively large monodisperse polymeric microspheres when relatively small colloidal particles bind to the former microspheres in an immunochemical reaction induced, proportionally to concentration, by an analyte. Examples of particle properties that can be monodispersed, as measured by flow particle analyzers, are: the so-called Coulter-volume of insulating particles in a given orifice diameter in an electrical impedance flow particle analyzer; the fluorescent emission by single particles when illuminated at a given wavelength, also in an optical flow particle analyzer; and, the light scatter properties of monodisperse microspheres substantially in a given direction when illuminated, e.g., in an optical flow particle analyzer. The last-named property is used in the present method to measure and detect one or more analytes in a single fluid sample.

In particular, the present inventors have discovered that the aforementioned colloidal particles by themselves do not scatter light in a manner which can be detected under the conditions used for the process. Even if the colloidal particles were to agglutinate with one another, as by virtue of reaction with nonspecific binding components found often in sera, they do not interfere with the assay. However, these colloidal particles cause profound changes in the statistical distribution of various light scatter signals generated from the monodisperse polymeric microspheres when the colloidal particles bind to the surface of the polymeric microspheres to form an immunocomplex. For example, where the polymeric microspheres are coated with a first complementary binding molecule and the colloidal particles are coated with a second binding molecule, a protein (i.e., antigen or antibody) or hapten analyte that is complementary to both first and second binding molecules will effectively crosslink the colloidal particles to the polymeric particles, and will bring about a change in the dimensions of the light scatter pulse height distribution histogram of the monodisperse polymeric microspheres compared to the control histogram dimensions obtained in the absence of colloidal particles and/or analyte. The aforementioned change in the histogram dimensions has been found to correlate directly with the amount of the analyte present in the fluid sample. The present inventors have also discovered that the aforementioned change in the histogram dimension occurs with only a slight shift in the position of the monodisperige polymeric microsphere light scatter pulse height distribution histogram, which indicates that self-aggregation of polymeric microspheres is not involved.

Figure 4A:
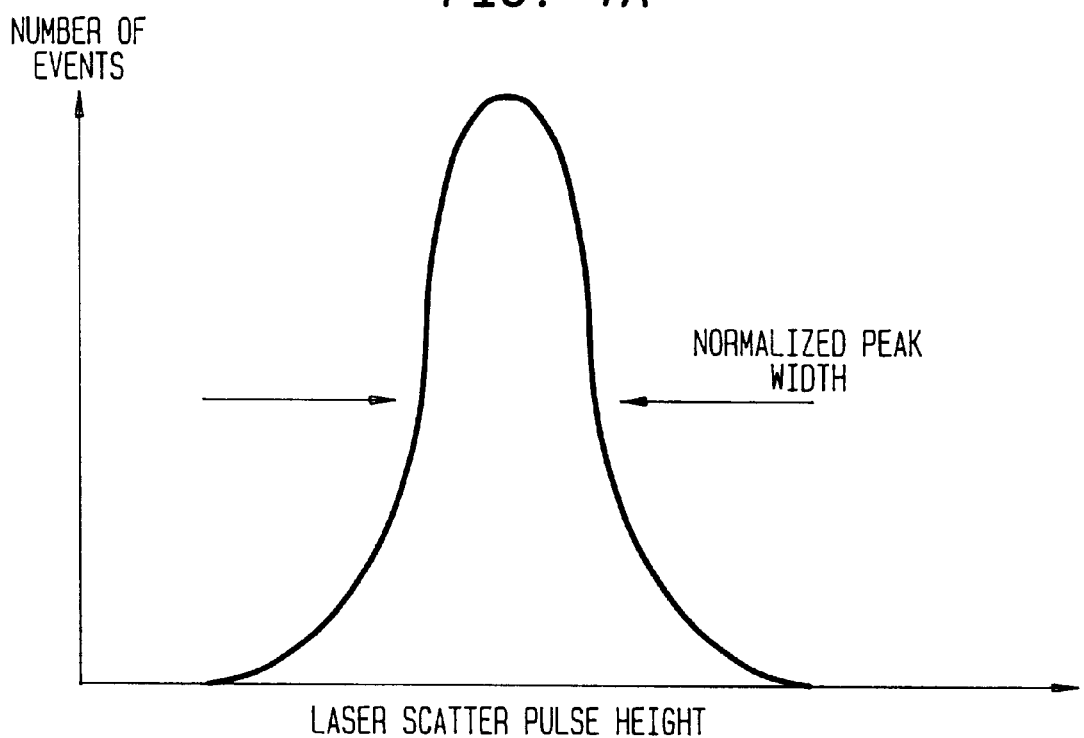
FIGS. 4A and 4B show the normalized peak width parameters and calibration (i.e., standard) curve, respectively, for a forward binding (i.e., sandwich) assay.

One preferred dimension for monitoring changes in the histogram is the peak width at one half peak height of the graphical representation of the detected light scatter pulse height distribution histogram. This dimension will be referred to in this specification as "normalized peak width" or "NPW" see FIG. 4A). The detection of analyte in each of the assay methods described below utilize this measurement. In the case of a forward binding (sandwich) immunocomplex formation method both the relatively large monodisperse microspheres and the relatively small polydispersed colloidal particles are coated with different complementary binding molecules. Where the analyte is an antigen or hapten, monodisperse polymeric microspheres are coated with a first complementary anti-antigen or hapten analyte antibody, which may be a monoclonal antibody, directed to a first epitope on the antigen. The polydisperse colloidal particles are coated with a second anti-antigen analyte antibody, which may also be a monoclonal antibody, directed to a second epitope of the antigen analyte. In the presence of antigen, a typical "sandwich" reaction takes place, with the antigen effectively crosslinking the smaller colloidal particles randomly on the surface of the larger polymeric microspheres. When this occurs, and the resulting particulate immunocomplexes are passed through the optical flow cell of FIG. 1, the CV and standard deviation of the monodispersed light scatter pulse height distribution histogram, as reflected in a graphical representation of the histogram, produces peaks that broaden approximately symmetrically about the peak mean. That is, the change in histogram dimension is a widening of the NPW in the graphical representation and, consequently, an increase in the coefficient of variation (CV) around the histogram mean. This broadening is directly and quantitatively related to the concentration of the analyte in the fluid sample.

Figure 2A:
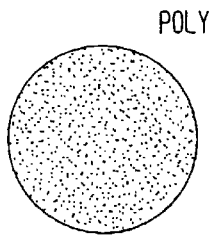
FIG. 2A shows polymeric microspheres and metal particles.
Figure 2B:
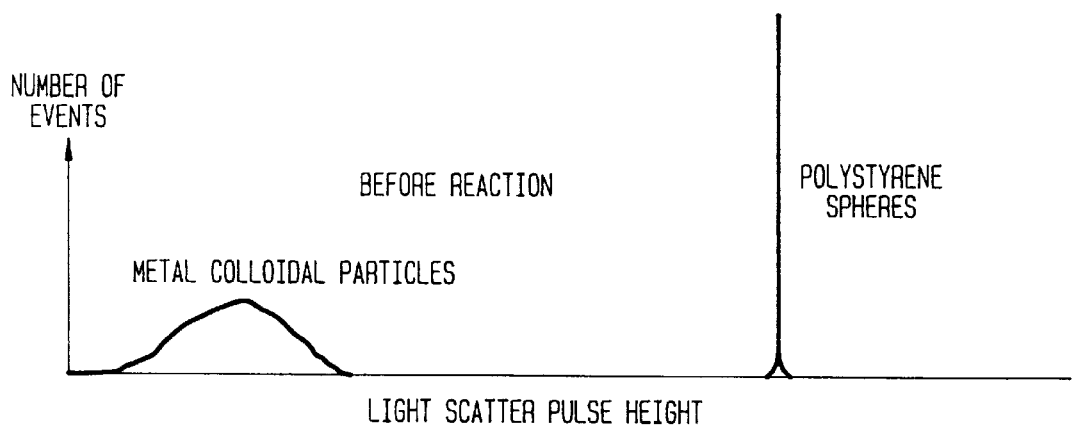
FIGS. 2B and 2C show light scatter pulse height distributions of the microspheres and the colloidal particles before and after binding of the colloidal particles to the monodisperse polymeric particles.
Figure 2C:
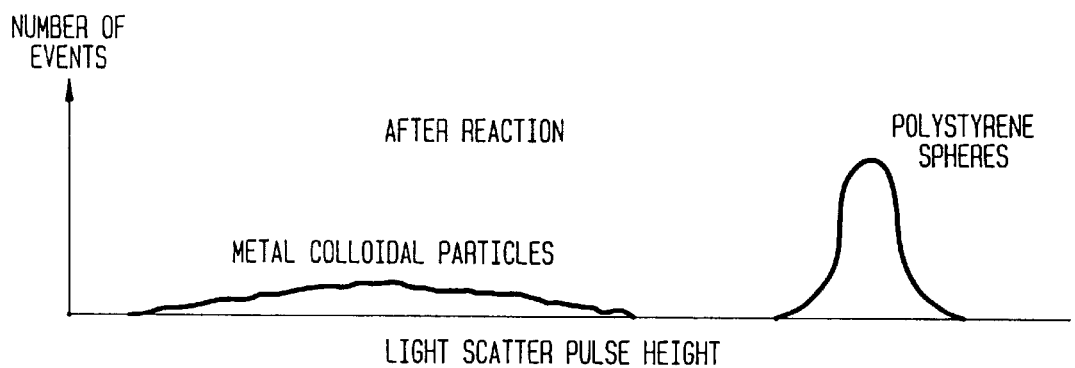

The principle of this embodiment of the invention is shown in FIGS. 2A–2D. In FIG. 2A are shown the relative diameters of monodisperse latex microspheres (about 1.0 μm diameter) and the polydisperse colloidal particles (about 20 to 120 nm in diameter). In the preferred particle diameters described above, it can be seen that the ratio of polymer microsphere diameter to colloidal particle size ranges between 15–30:1. This characteristic provides the potential for a large number of colloidal particles to be bound randomly on each polymeric microsphere. The light scatter pulse height distribution histogram for the latex microspheres is shown in FIG. 2B. The pulse height signal from the latex microspheres is high, and the width of the peak representing the histogram is very narrow. As is evident, the small amount of light scatter from self-agglutinated metal particles does not interfere, i.e., does not overlap, with the histogram produced by the microspheres. After analyte-mediated binding of the colloidal particles to the latex microspheres, a broadening of the latex histogram peak occurs (FIG. 2C) in a forward binding reaction. Even when multiple analytes in a single sample are analyzed simultaneously by a combination of the present embodiments (histograms D1, D2, D3 and D4 in FIG. 2D), there is no overlap with the signal generated by unbound gold particles.

The measurement of statistical changes in the dimension of a light scatter pulse height distribution histogram can be the basis for a quantitative determination of an analyte in a fluid sample in displacement-, competition- and inhibition-type immunoassay methods.

To conduct a displacement assay, the two types of particles are first immunochemically sensitized by incubation separately with complementary binding molecules to form a two component immunocomplex reagent. In one embodiment, the large polymeric microspheres are coated stably with analyte. The colloidal particles are coated with a binding molecule such as an anti-analyte antibody that is complementary to the analyte. The two suspensions are mixed to form an immunocomplex reagent that may be stored prior to use. A base line determination of the light scatter pulse height distribution histogram of this reagent will show a dimension that resembles that which results when the two types of particles are immunocomplexed, that is, a wide NPW if this is the dimension examined. When this reagent is mixed with a fluid sample containing an analyte that is complementary to the binding molecule with which the colloidal particles are coated, the colloidal particles will be displaced from the immunocomplex reagent in direct proportion to the concentration of analyte present, and the histogram dimension will return to that resembling control monodisperse polymeric microspheres. That is, the dimensions of the histogram, i.e., the NPW (and CV) will be reduced. The statistical extent of dimension reduction, as reflected in the NPW, can be correlated by standard means to the concentration of analytic in the fluid sample.

In a competition embodiment, first binding molecule-coated monodisperse polymeric particles and analyte compete for binding to second binding molecule-coated colloidal particles. The NPW for the polymeric particles is inversely related to the concentration of fluid sample being analyzed. That is to say, a high analyte concentration will "capture" a relatively larger fraction of the colloidal particles, leaving a relatively smaller fraction of colloidal particles to bind to the polymeric microspheres. This will produce a relatively narrow histogram, i.e. a small NPW as compared to a control which in this embodiment is the coated polymeric particles. As in the previous two embodiments, the analyte may be an antigen, hapten, antibody or nucleic acid, and it is well within the skill of the assayist, following the guidelines provided by the invention, to select appropriate binding molecules with which to coat the microspheres and colloidal particles.

In an inhibition embodiment, the analyte-containing sample is incubated with anti-analyte antibody-coated colloidal particles for a finite time, e.g. 5–30 minutes, which does not necessarily include the time necessary tea reach equilibrium, which may be on the order of hours. During this period, the analyte binds to and sequesters a portion of the colloidal particles. Analyte-coated monodisperse polymeric microspheres are then added and incubation is continued for another finite time, which is of the order of about 5–10 minutes. During this period, the analyte inhibits the binding of colloidal particles to the polymeric microspheres because the analyte has sequestered the colloidal particles. Histogram dimensions of both the control and bound microspheres are determined as above. High concentrations of analyte will produce narrow histogram peak widths as the result of its sequestering of the colloidal particles; low concentrations of analyte will produce widened histogram peak widths. That is, the amount of unbound colloidal particles is inversely related to the concentration of the analyte in the sample.

The incubation mixtures mentioned above need not be stirred during reaction periods. When adding components of reaction mixtures, only brief mixing (1–2 seconds) to produce homogeneity of the mixture is required. This may be achieved in some cases by simply adding the constituents to the flow particle analyzer. Both homogeneous and heterogeneous assays may be conducted in accordance with the present invention. In the case of a heterogenous assay, the immunocomplex and any uncomplexed microspheres are separated from the reaction mixture prior to the step of illuminating. Typically, the separated microspheres are resuspended in a liquid phase to provide a new mixture which is then passed through a flow particle analyzer. Of course, in a homogeneous assay, the phases are not separated and the reaction mixture itself is passed through the flow particle analyzer.

The various embodiments of the methods of the present invention have been described in terms of generating NPWs of the histogram of the light scatter pulse amplitudes from complexed monodispersed microspheres. These light scatter signals are generated by the passage of particles (e.g., complexed or uncomplexed microspheres) through the viewing zone and are typically measured at low angles in the forward direction from about 3 to about 7 degrees from the axis of the incident beam. However, the presence and amount of a given analyte in a sample also can be determined from measurements of the light scatter signals at other angles, ranging from substantially side-scatter signals (from about 85 to about 95 degrees from the axis of the incident beam) to back scatter signals (from about 95 to about 180 degrees from the axis of the incident beam). Further, the light scatter pulses may be characterized by measuring their amplitudes, widths, or integrated pulse areas, or some linear or non-linear function of these parameters at the same or different scattering angles. For example, the scatter signature may represent the product of the pulse amplitude and pulse width, both measured at low forward angles. Another example of a scatter signature (characteristic) is the ratio between the amplitude of light scatter pulses at low forward angles and the integrated pulse area of light scatter pulses measured at 90 degrees. The scatter signature may also be represented by the angle to the incident beam at which the intensity of light scattered by the particles is at a maximum.

In addition, the determination of a statistical distribution of the changes in light scatter characteristics has been described in each of the embodiments in terms of the generation of a histrogram and measurement of normalized peak width NPW. However, such determination can be made in accordance with other known statistical procedures. For example, the determination of the statistical distribution may include essentially any measure of variance of the signals, for example, the standard deviation of the light scatter signals or the proportion falling within a certain range.

While it has been convenient to describe the forward binding (sandwich) reaction, inhibition, displacement and competition embodiments of the invention in terms of an antigenic or hapten analyte and antibody-coated particles, it should be understood that the scope of this invention includes assays in which the analyte is an antibody present in, for example, human or animal serum and the like. In such assays carried out in the forward binding mode, both types of particles may be coated with the antigen that is complementary to the analyte or, optionally, one type of particle may be coated with the antigen and the other with a second antibody directed against the antibody analyte. In this mode, in the presence of the antibody analyte, the small colloidal particles will form a complex with the monodisperse particles, and the above described changes in the statistical distribution of the measured light scatter property will be determined.

The foregoing has described assaying for a single analyte in a fluid sample. It is within the scope of this invention to analyze concurrently multiple analytes in the same fluid sample without the need to split the sample for multiple assays as must be done in prior art methods. This may be accomplished by selecting for each analyte to be determined a microsphere having a unique diameter and/or refractive index such that the light scatter signal from each type of microsphere is resolvable from the others. For example, in an amplitude-based system, the scattered light amplitudes for one type of particle may be several times that for another type. A type of binding reaction is also selected for each analyte. The coatings on the different size microspheres will, of course, be determined by the type of assay system to be assigned to the analyte, e.g., forward binding, inhibition, displacement or competition.

The assay systems for the multiple analytes may be the same or different. This embodiment of the invention relies upon the electronic components of the FPA to monitor the light scatter signals produced by each differently sized microsphere. Electronic systems for separating and monitoring light signals from each of several sizes of microspheres simultaneously present in the sample are disclosed in copending U.S. patent application Ser. No. 883,574, now U.S. Pat. No. 5,286,452, herein incorporated by reference in its entirety. In this regard, the aggregation of the colloidal microparticles with each type of microsphere, or the absence of such aggregation, will alter the distribution of the light scatter signals for each type of microsphere about the mean for that type. However, the changes will not cause the values of the signals for the different types to overlap. Thus, signals from each type of microsphere can be separated from signals from other types, and the distribution of signals within each type can be measured. Briefly, signals from light detectors that receive the light scatter signals from microspheres may be analyzed by either of two analytical systems. In a preferred analytical system which is software based, pulses from the light scatter detector are fed to an analog-to-digital converter which samples the peak height or other signal value of each pulse and passes these peak height values to a computer which sorts the peak height or other values by magnitude and then arranges them in a distribution for each analyte. For example, the system may form a histogram, which may be a smoothed histogram, one for each analyte.

A variety of commercially available monodisperse microspheres may be used in this invention. Suitable materials to prepare the monodisperse microspheres include synthetic, e.g., polymeric materials such as nylon, glass, and microscopic oxide powders. Synthetic polymers, particularly uniform latex microspheres, are highly preferred. Bangs, L. B., *Uniform Latex Particles*, Seragen, Indianapolis, 1984. Although the term "latex", strictly speaking, refers to the polyisoprene of which milk sap its composed, the definition of this term has been expanded, and will be used herein to include synthetic polymers such as polybutadiene, polystyrene and the like. Uniform latex microspheres of average diameter ranging between 0.25 and 10 $\mu$m, preferably between about 0.5 and about 5.0 $\mu$m, and having stable hydrophobic surface groups to which proteins bind strongly so as to produce stable hydrophilic colloidal suspensions, are preferable diameters for use in the invention, although diameters ranging up to about 100–120 $\mu$m are available commercially. The 0.5 to 5.0 $\mu$m diameter latex microspheres with highly monodispersed diameters are available from Polysciences, Inc., Warrington, Pa. 18976 and from Interfacial Dynamics Corp., Portland, Oreg. 97220. The standard deviation of diameters expressed as percent of the mean (i.e., coefficient of variation, or CV) are approximately 1% to 2% for these commercial preparations, and it is most preferred that CV's of 2% not be exceeded.

Binding molecule-coated microspheres may be purchased commercially (Polysciences, Inc.) or prepared as described in Seaman, G.V.F., ed., Latex Based Technology in Diagnostics, Health & Science Communications, Washington, D.C. 20005, 1990, which is incorporated herein by reference. In a typical coating procedure, suspensions of microspheres are incubated with a buffered (pH 4 to 10) solution of a first binding molecule at a concentration and for a period of time (typically, 0.5 to 16 hrs) sufficient to reach equilibrium binding of the molecule to the microspheres. Coated microspheres are recovered by brief centrifugation, and nonspecific binding sites blocked by a brief (e.g. 15 min) exposure to a solution of an inert protein (e.g., nonfat dry milk solids or serum albumin). Coated microspheres are then washed at least three times with at least a 4-fold volume of cold storage buffer. Any storage buffer that provides stability to the microsphere suspensions on storage may be used. Typical storage buffers are 0.5% BSA-0.1% $NaN_3$ in 0.154 M NaCl, pH 7.4, or 0.1% BSA-0.01% $NaN_3$ in 10 mM HEPES buffer, pH 7.5.

The colloidal material preferably contains particles including metals and metal compounds, such as metal oxides, metal hydroxides and metal salts. Preferred examples of metals include gold, platinum, silver and copper. Gold is highly preferred. Methods of production of colloidal gold of the desired range of particle diameters, and methods for coating metal particles with proteins, are described generally in European patent application 426,300, Roth, J., "The Colloidal Gold Marker System for Light and Electron Microscopy Cytochemistry", in Bullock, G. R. et al., *Techniques in Immunocytochemistry* 2:217 (1983), in Horisberger, M., *SEM* 11:9 (1981), in Weiser, H. B., Inorganic Colloid Chemistry, J. Wiley, N.Y. 1931, p. 1, in Leuvering, J. H. W., U.S. Pat. No. 4,313,734, and in Frens, G., *Nature, Physical Science*, 241:20 (1973), all of which are incorporated by reference.

Polydisperse colloidal gold particle suspensions may be used. They may be obtained from E-Y Laboratories, Inc., San Matteo, Calif. 94401 or prepared as described in the above-cited references. In a preferred method, polydisperse colloidal gold particles of particle size 10 nm to 120 nm diameter are produced by the method described in EPA 426,300. As noted above, gold particles of such sizes do not produce measurable and interfering light scatter under the conditions of the invention. Within the present context, therefore, by "polydisperse metal particles" is meant a population of colloidal metal particles whose diameters range between 20 nm and 120 nm. However, non-polydispersed or monodispersed colloidal particles can also be used.

Applicants have further found that colloidal particles, when used at high densities relative to microspheres such as from 2 to 100,000 to 1, act as "scavengers" for nonspecific interfering substances commonly found in fluid samples of biological origin, such as human serum. That is to say, the colloidal particles not only provide the basis for the quantitative immunoassay of the invention, but also reduce the deleterious effects of interfering substances. Although the useful particle ratio in this regard is very broad, colloidal particle to microsphere ratios of the order of 1,000 to 10,000:1 are preferred.

Figure 3:
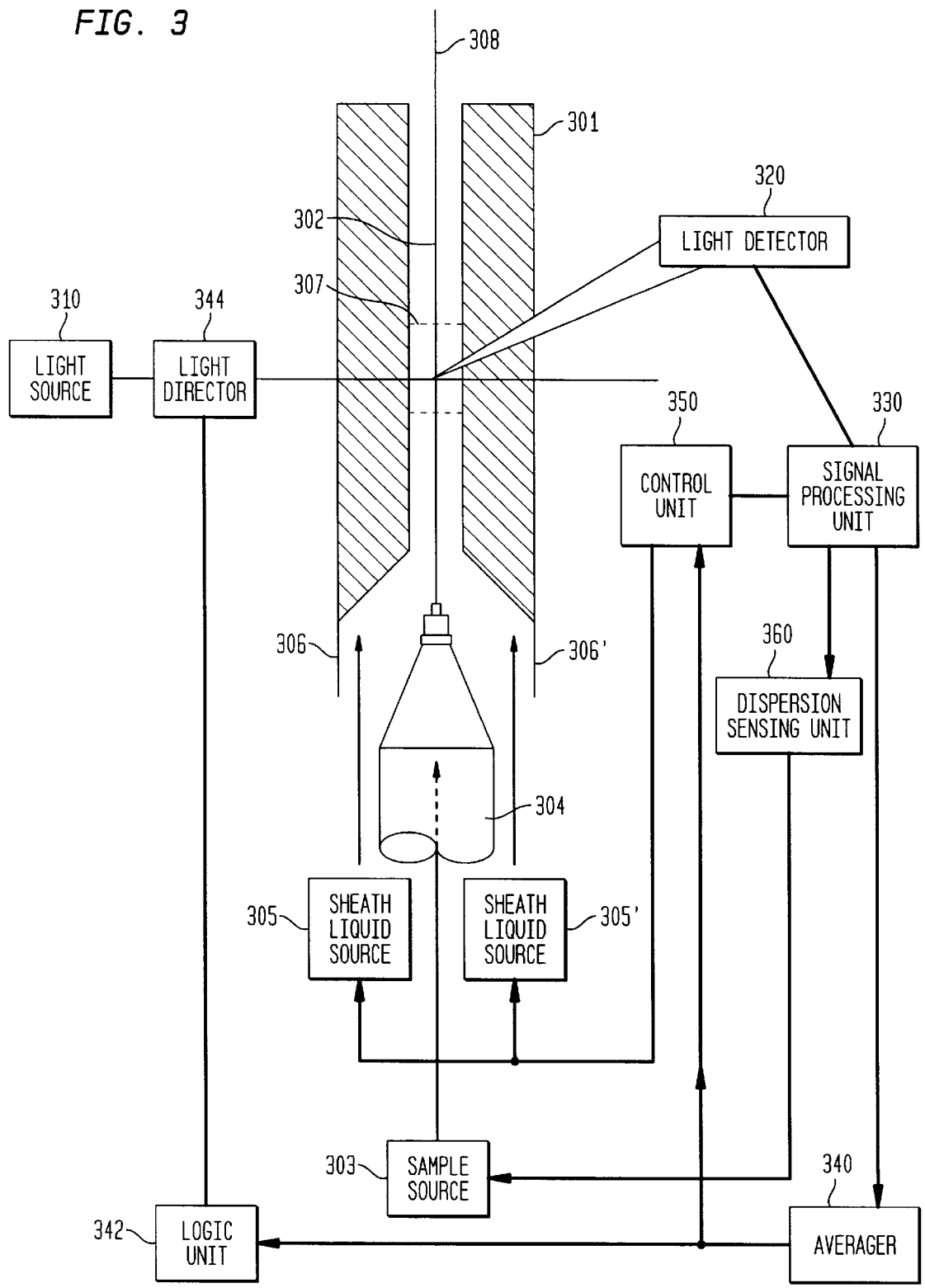
FIG. 3 illustrates a schematic view of an optical flow particle analyzer according to the present invention.

FIG. 3 illustrates a schematic view of an optical flow particle analyzer according to a further embodiment of the present invention. Flow cell 301 defines a central bore 302. Central bore diameters will generally range between 100 $\mu$m and 500 $\mu$m. A diameter of about 250 $\mu$m is preferred. Sample source 303, sample entrance port 304, sheath liquid sources 305 and 305', sheath liquid entrance ports 306 and 306', viewing zone 307 and light source 310 are substantially as described in relation to FIG. 1, above. However, an automatically operable light director 344, is interposed between source 310 and cell 301. Director 344 incorporates connecting adjustable optical elements, such as one or more lenses or mirrors, actuated by driving elements such as servomotors and piezoelectric elements. Director 344 is adapted to maintain the light beam from source 310 in directions perpendicular to the bore 302 of cell 301 to shift the relation positions of the beam and bore. Also, sheath liquid sources 306 and 306', as well as sample source 303, are controllable flow rate devices such as stepper-motor driven syringe pumps, gravity or pressure driven feed devices with motor-controlled valves or variable driving pressure or vacuum activated devices. The sheath liquid sources are arranged so that source 306 provides sheath liquid principally on the side of the bore to the rear of the drawing as seen in FIG. 3, whereas source 306' provides sheath liquid principally on the side of the bore to the front of the drawing as seen in FIG. 3.

The light scattered from particle stream 308 is detected by light detector 320, and the signals are then analyzed by the signal processing unit 330. The signal processing unit ultimately makes a determination of the statistical changes in the specific light scatter property. It also performs several monitoring functions in conjunction with averager 340, control unit 350, and dispersion sensing unit 360. Averager 340 processes amplitude signals received from the signal processing unit. The averager calculates the mean amplitude of the individual pulses of scattered light detected by the light detector, and passes this information to logic unit 342. Logic unit 342 controls light director 344 to adjust the relative position of the beam such that the light emitted from the light source produces scattered light having a maximum amplitude.

This will occur when the beam centerline crosses the bore centerline; at other positions, the amplitude is lower. During a position-finding cycle, logic unit 342 actuates director 344 to a plurality of different positions, records the average amplitude for each position and then selects the position which yields the greatest average amplitude. This position is then employed during the actual measurements.

The CV of the light scatter pulse height distribution histogram obtained from particles such as the microspheres discussed above is a strong function of the relative diameter of the sample stream through the flow cell of the FPA and the focal dimensions of the incident (e.g., laser) light. If the sample stream is relatively large, then particles can flow through different intensities of the incident light beam and yield an undesirably large CV of pulse heights, even though the CV of the particles themselves may be small. Thus, it is preferred to center the fluid sample stream and to confine it to a diameter range of about 3 $\mu$m to 10 $\mu$m. In a highly preferred system, this diameter amounts to about 1% to 3% of the width of the laser light beam. Under these conditions, CV values for light scatter pulse height distribution histograms of less than 2% for monodisperse polymeric microspheres can be obtained, and are most preferred. Those skilled in the art will appreciate that the sensitivity of a given assay will vary inversely with the CV of the monodisperse microspheres. Accordingly, as used in the present context "monodisperse" is taken to mean a population of polymeric microspheres that produce a low angle forward scattered light pulse height distribution histogram with a CV value sufficient to meet the sensitivity requirements of a given assay, wherein the CV is preferably no greater than about 5% and more preferably about 2% when measured under the preferred conditions stated above. CV's less than 2% are most preferred.

Dispersion sensing unit 360 determines the CV value of signals that are received from signal processing unit 330, and adjusts the rate of flow of the sample liquid from source 303, to control the diameter of the sample fluid stream in the center of bore 302. As stated above, it is preferred that the dimensions of the particle bearing sample fluid stream are of the same order of magnitude as the maximum dimension of the particles being carried by the stream. Where the sample fluid stream substantially exceeds these dimensions, the CV of the signals will increase substantially. Dispersion sensing unit 360 is actuated while the sample fluid includes particles of known dispersive properties, desirably monodisperse particles such as unreacted microspheres. If the CV of the signals is above a preselected maximum level, the dispersion sensing unit actuates the sample source 303 to reduce the sample flow, and thus narrow the sample stream, until the dispersion is below the preselected maximum level. Alternatively, the dispersion sensing unit actuates sheath liquid sources 306 and 306' to increase sheath liquid flow rate which in turn narrows the sample stream.

To regulate both the narrowing and centering features, the sample stream can be monitored before, after and during the times during which the immunoreacted particles are measured. This can be accomplished in either case with a control population of monodisperse polymeric microspheres of the same or different diameters as that of the analytical microspheres and that do not participate in any immunobindinig reactions.

Where the sample fluid includes unreacted, monodisperse polymeric control microspheres of one diameter and binding-molecule coated test microspheres of substantially different diameter, the signals from the control microspheres can be segregated by signal processing unit 330. Only the control microsphere signals are used to actuate the beam positioning, stream centering and sample stream flow control devices. The apparatus configuration car be varied substantially. For example, the light directing device 344 can be replaced by a device for physically moving cell 301 while the beam remains in fixed position. Also, one or more of the adjusting devices can be omitted.

In an alternative embodiment, the sheath liquid sources 306 and 306' may be arranged such that the sheath liquid flows from the source radially inwardly with respect to the bore. In addition, the flow cell may be constructed in various shapes, e.g., rectangular.

The following examples are provided merely to illustrate several embodiments of the invention, and are not intended to delimit the scope of the invention which is encompassed by the specification and included claims.

EXAMPLE 1

FORWARD (SANDWICH) BINDING REACTION ASSAY FOR SERUM THYROID STIMULATING HORMONE TSH

Polydisperse colloidal gold particles (50–80 nm) were coated with a first anti-TSH monoclonal antibody (BioDesign International, Inc., Kennebunkport, Me. 04046) as follows. A suspension of colloidal gold particles was brought to pH 7.5 using 0.2 M potassium carbonate. To this suspension was added a 0.1 volume of the coating antibody diluted in 10 mM HEPES-0.02% BSA, pH 7.5. After mixing for 1 hr, a 0.1 volume of a solution of non-fat dried milk solids were added with mixing to block non-specific binding sites. The particles were washed three times by centrifugation in 10 mM HEPES buffer (pH 7.5) containing 1% BSA, 0.01% $NaN_3$ and 1% mannitol.

Polystyrene (latex) beads of 1.62 $\mu$m diameter (approximate diameter CV of 2.0%) (Interfacial Dynamics Corp.) were coated with a second anti-TSH monoclonal antibody as described in Hansen, U.S. patent application Ser. No. 883,574, U.S. Pat. No. 5,286,452.

Figure 4B:
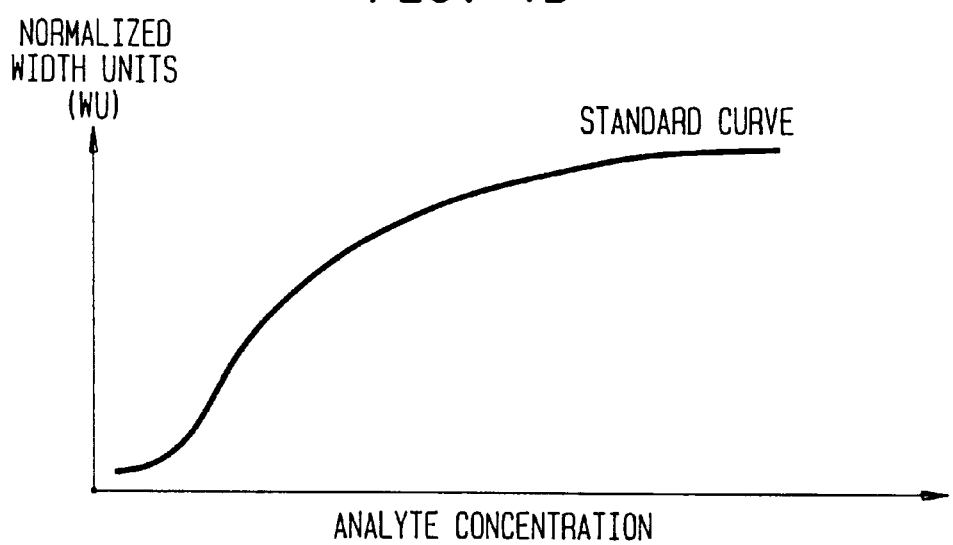
Figure 5B:
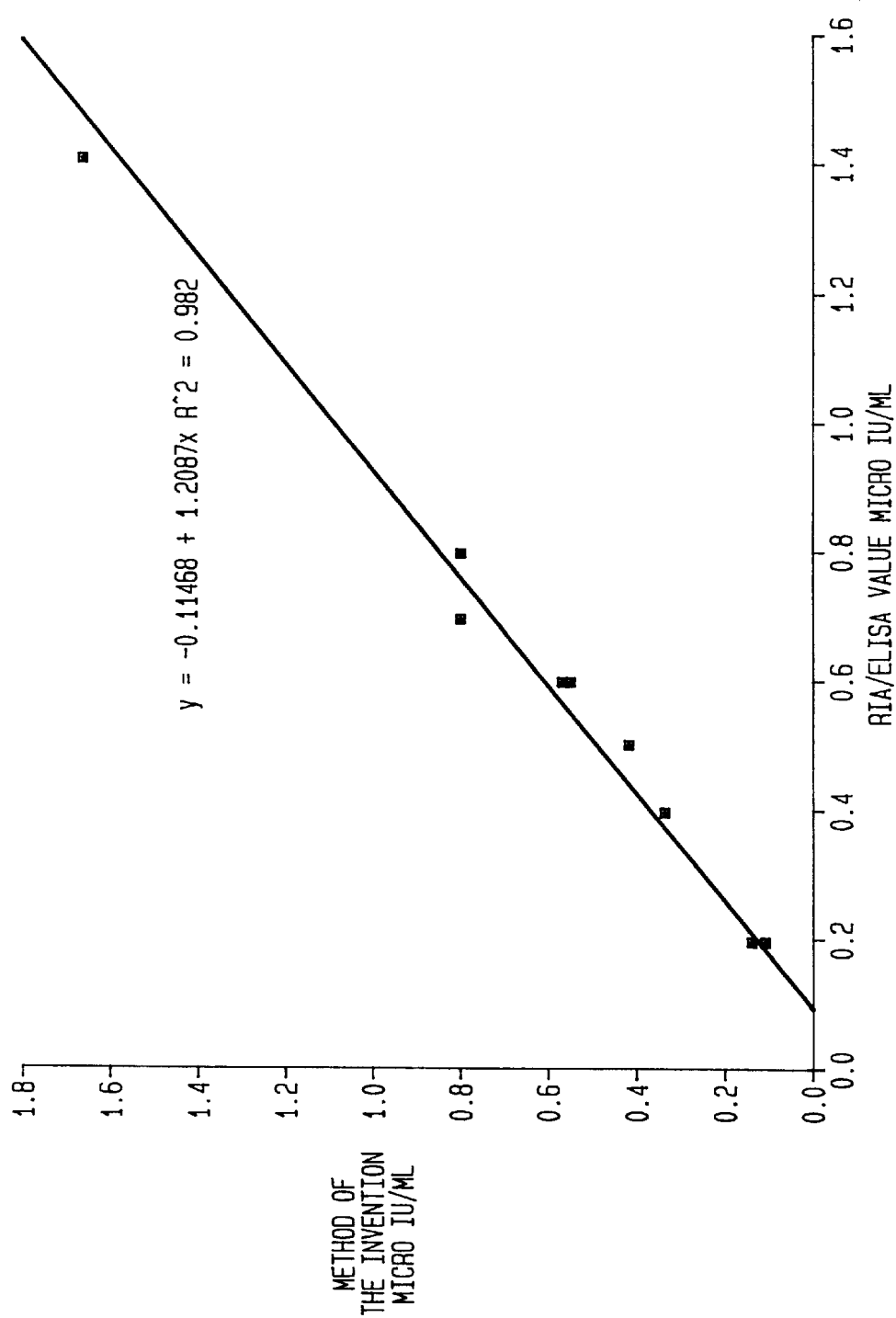
FIG. 5B shows a comparison with other methods.

Coated gold particles were mixed with coated latex particles in a ratio of 10,000 to 1 to form Reagent A. Reagent A was added to TSH-containing serum in a volume such that the final latex microsphere density was about $2 \times 10^6$/mL, and the serum was 40%. After 60 minutes of incubation at room temperature, the mixture was measured in a sheath FPA as described above using low angle forward light scatter. Normalized peak width (NPW) units (illustrated in FIG. 4A as a function of the number of events and individual pulse height, and in FIG. 4B as a function of analyte concentration) as a function of analyte TSH concentration in the serum over the concentration range of 0 to 1.2 $\mu$IU/mL is shown in FIG. 5a. FIG. 5b illustrates a linearized interpretation of the TSH assay compared with an RIA/ELISA. The data extrapolates to a sensitivity of about $5 \times 10^{-13}$ M in serum. The presence and amount of other multi-epitopic antigens can be determined in accordance with this procedure.

EXAMPLE 2

INHIBITION ASSAY FOR THYROXINE (T4)

Monodisperse latex microspheres (1.62 $\mu$m diameter, Interfacial Dynamics Corp.) were coated with human thyroglobulin (Calbiochem Inc.) as follows to form Reagent A. The microspheres were incubated overnight with antigen thyroglobulin in 10 mM HEPES buffer, pH 7.5. Microspheres, recovered by centrifugation, were washed with HEPES buffer containing BSA and $NaN_3$ as described above, and stored in the same buffer containing mannitol.

Polydisperse colloidal gold particles (50–80 nm diameter) were coated with an antibody to T4 as follows to form Reagent B. One-tenth volume of 10 mM HEPES buffer (pH 7.5) containing antibody and BSA was added to the gold particles. For the T4 assay, an IgG-purified polyclonal antibody specific to T4 (OEM Concepts) was used for coating. Coated particles were then post-coated with a solution of non-fat dry milk powder to block nonspecific binding sites. Particles were recovered by centrifugation and washed with 10 mM HEPES buffer (pH 7.5) containing BSA and $NaN_3$. Washed particles were stored to the same buffer, to which mannitol was added as a stabilizer. Coated gold particles were diluted into an assay buffer containing 50 mM glycine (pH 9), 10 mM EDTA, 0.01% aminonaphthosulfonic acid (Sigma Chem. Co., St. Louis, Mo.), 0.1% BSA, 0.3 M KI and 0.01% $NaN_3$.

Serum samples containing $^3$T4 were incubated with Reagent B for 30 minutes, and then Reagent A was added to deliver a microsphere density of $2 \times 10^7$/mL. After an additional 30-minute incubation, samples were analyzed in the FPA for histogram peak width determination using low angle forward light scatter.

Figure 6A:
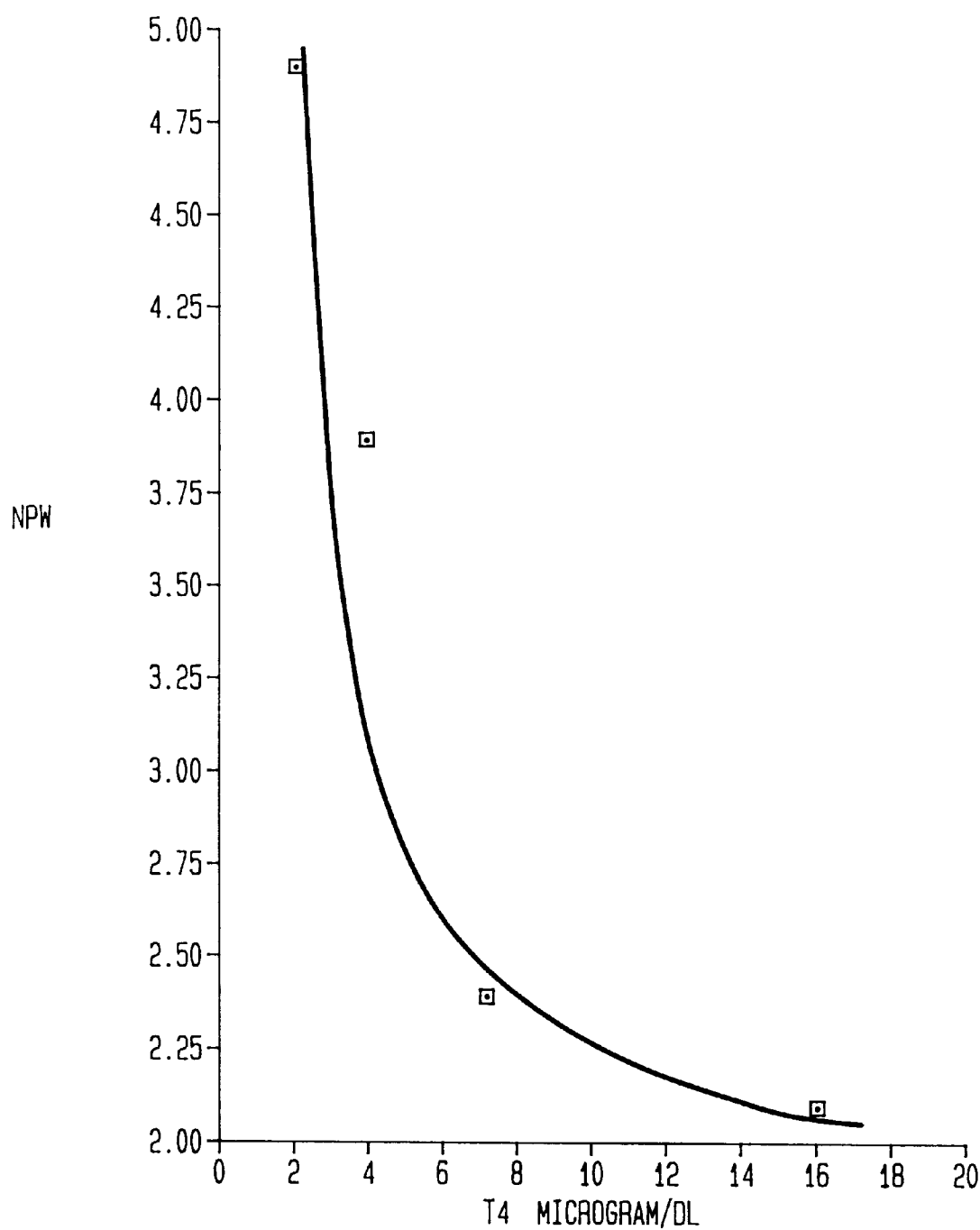
FIGS. 6A and 6B show a T4 standard curve and a comparison with other methods, respectively, in human serum.
Figure 6B:
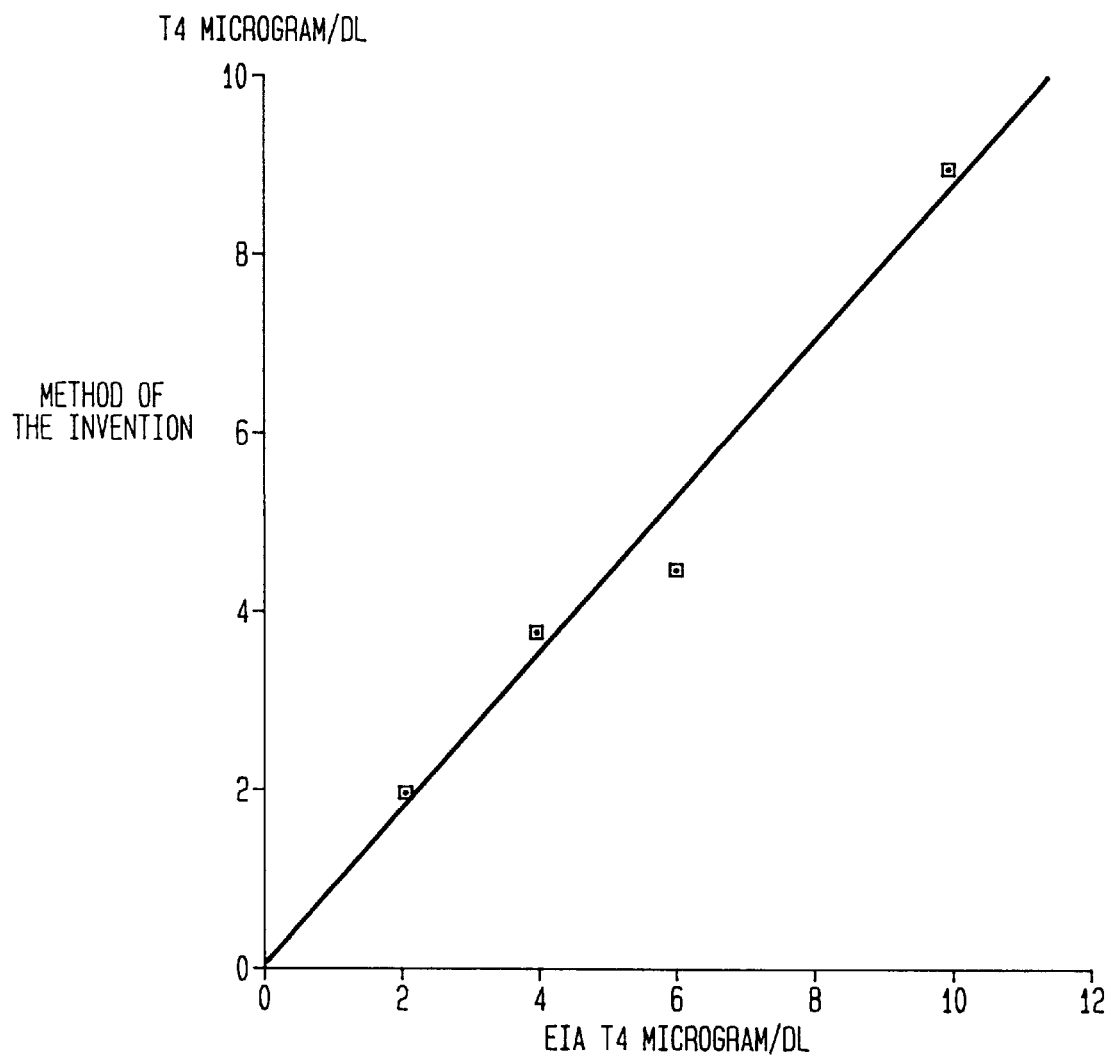

Serum T4 inhibits the binding of gold particles with latex thyroglobulin. As illustrated in FIG. 6A, high concentrations of serum T4 produced narrow histogram peak widths, and low concentrations of serum T4 produced the converse. The curve in FIG. 6A was generated using calibrator sera (Biomerica, Inc., San Luis Obispo, Calif.) and served as the standard curve for further comparisons with standard EIA methods, i.e., the EMIT method (Syva Corp., Palo Alto, Calif.). The correlation data are shown in FIG. 6B. The correlation was>95% over the analyte concentration rangre shown.

EXAMPLE 3

SIMULTANEOUS ASSAY OF TSH AND T4 IN THE SAME FLUID SAMPLE

The TSH and T4 immunoassays described in Examples 1 and 2 were combined in order to demonstrate that multiple analytes may be analyzed in the same fluid sample. The T4 and TSH assays were carried out with monodispersed latex microsphere populations having mean diameters of 0.95 $\mu$m and 1.62 $\mu$m, respectively. The final serum concentration was 15%, the gold particle concentration was $1 \times 10^{10}$/mL, and the latex microsphere concentrations were $1 \times 10^8$/mL for T4 and $5 \times 10^6$/mL for TSH.

Reactions were carried out in the following sequence. The TSH-assay reaction was performed as described in Example 1. After 30 minutes of this reaction, Reagent B of Example 2 was added. Twenty-five minutes thereafter, Reagent A of Example 2 was added and the mixture incubated for five minutes. FPA analysis was then performed.

When midrange concentrations of the analytes were assayed with the FPA system and methods of the present invention, the results were 4 $\mu$g/mL for T4 and 2 $\mu$IU/ml for TSH. When a sample with no T4 and a TSH midrange level of 2 $\mu$IU/mL was assayed by the present method, the measured T4 value was zero, and the measured value for TSH was 2 $\mu$IU/mL±10%. With a sample with a known low value for TSH (0.3 $\mu$IU/mL) and a known midrange value of 4 $\mu$g/mL for T4, the present method correlated within 10% with the known values.

This experiment demonstrates the way in which the present invention permits simultaneous assays can be performed with separable results, and with no detectable cross-interference between assays in a single run.

EXAMPLE 4

COMPARISON OF THE PRESENT METHOD WITH A STANDARD LATEX-LATEX AGGLUTINATION METHOD FOR IgE DETERMINATION

In order to demonstrate the efficacy of the present invention in suppressing the adverse effects of non-specific binding, an assay for human IgE was conducted in two formats. In the first format, ordinary latex microsphere-latex microsphere agglutination was carried out with anti-IgE polyclonal antibodies passively coated on the latex particles, according to the method of Masson et al., above, in which the disappearance of monomeric particles is monitored. The latex particle diameter was 1.62 $\mu$m. The second format consisted of the forward binding reaction embodiment of the present invention.

To coat gold particles, a suspension of gold particles was titrated to pH 7.5 with 0.2 M $K_2CO_3$. To this suspension was added a one-tenth volume of mouse monoclonal anti-human IgE (Biodesign International, Inc., Kennebunkport, Me., 04046) in 10 mM HEPES buffer, pH 7.5, containing 0.02% BSA. After 60 minutes of mixing, a one-tenth volume of 0.1% non-fat dried milk solids solution was added. The particles were isolated by centrifugation washed three times with the same buffer, then stored in a storage buffer consisting of 10 mM HEPES, 0.01% BSA, 0.01% $NaN_3$ 1% mannitol.

To coat latex microspheres, 1.62 µm latex microspheres (Interfacial Dynamics Intnl., Portland, Oreg. 97220) were diluted to a density of 0.5% in 10 mM HEPES, pH 7.5, the suspension was incubated overnight at 4° C. with a 100 µg/mL solution of affinity-purified goat anti-human IgE, microspheres were isolated by centrifugation and washed three times with HEPES buffer, and finally stored in 10 mM HEPES 0.1% BSA, 0.01% $NaN_3$ 1% mannitol.

For assay, latex and gold particles were diluted to $1 \times 10^8$/mL and $2 \times 10^{10}$/mL, respectively, in assay buffer. A 50 µl aliquot of analyte serum sample was added to 450 µl of the particle mixture, and mixed by vortexing; the final serum dilution was 10%. After 15 minutes of incubation at 23° C., the reaction mixture was subjected to FPA analysis. The assay buffer was 0.05 M glycine 0.1% BSA, 0.3 M KI, 0.0% $NaN_3$, pH 9.5.

A commercial ELISA IgE assay method for serum IgE (Ventrex Laboratories, Portland, Me.) served as the reference standard for both formats. The correlation curve for the latex-latex agglutination format is shown in FIG. 7A and that for the method of the invention in FIG. 7B. It is clear from the data that the correlation is poor and that the sensitivity is limited for the latex agglutination method, likely due to the influence of interfering substances in the analyte serum sample. In sharp contrast, the latex microsphere-gold particle method of the present invention shows an excellent correlation with the reference method (FIG. 7B).

EXAMPLE 5

KINETICS OF HISTOGRAM PEAK WIDTH BROADENING

Figure 8:
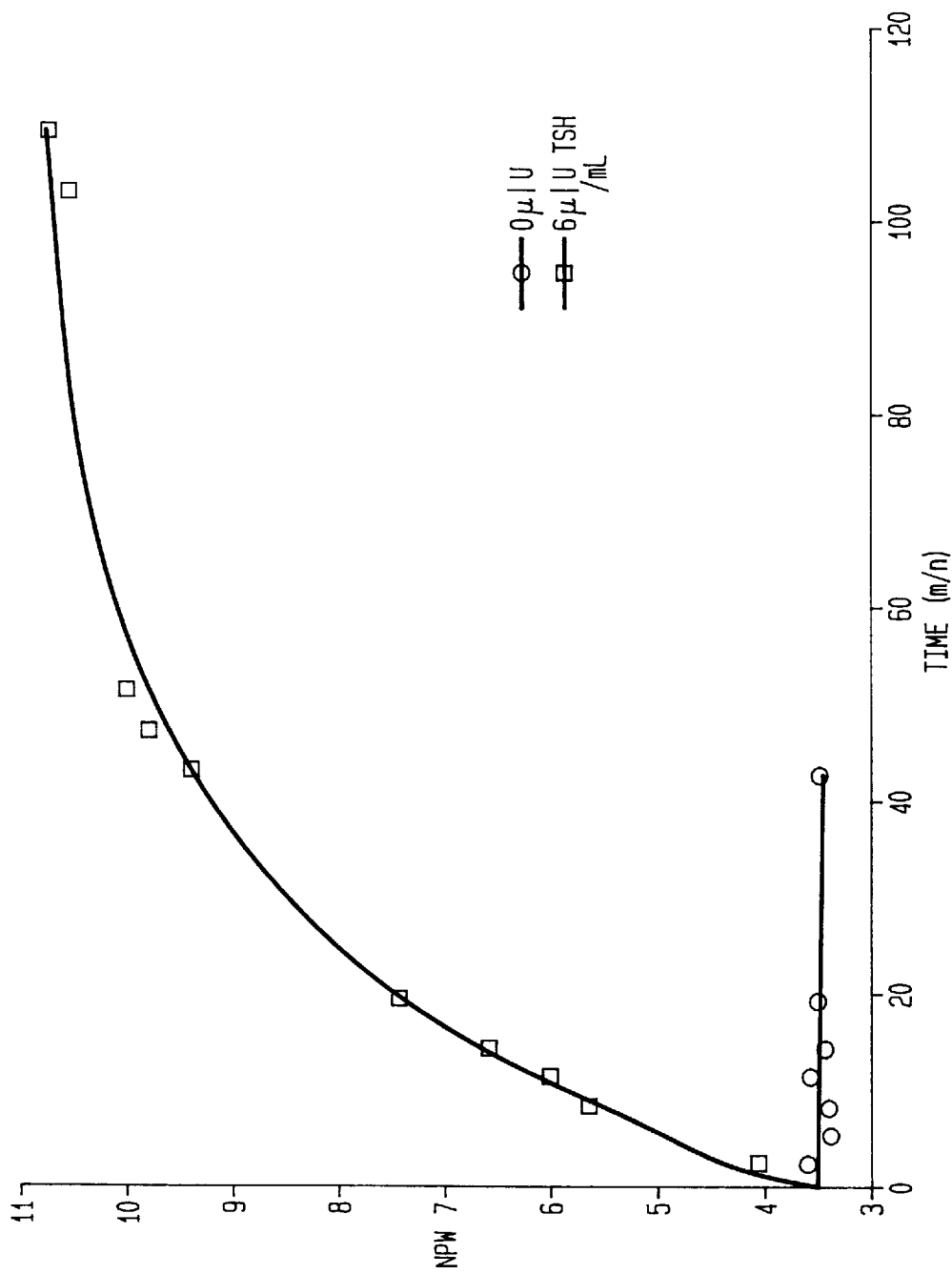
FIG. 8 shows the kinetics of binding of colloidal gold particles to latex microspheres brought about by the analyte TSH.

The assay of Example 1 was carried out in a manner that permitted low angle forward light scatter FPA analyses of the reaction mixture (containing 6 µIU/mL TSH) at progressive time intervals. The results are illustrated in FIG. 8. In the absence of analyte (-○-, FIG. 8), coated gold particles did not bind to coated latex microspheres, and there was no change in histogram dimension. However, in the presence of analyte (-□-, in FIG. 8) binding was detected from the first time point ts 2 min.), as reflected by a broadening of the histogram derived from the monodispersia latex microspheres. This broadening continued at a linear rate for the first 20 minutes of reaction, and reached a plateau at about 100 minutes.

We claim:

1. A particle light scatter-based immunoassay for measuring an analyte in a fluid sample, comprising steps:
   (a) combining with said fluid sample a reagent set including first binding molecule-coated monodisperse microspheres and second binding molecule-coated colloidal particles smaller than said microspheres, or an immunoconiplex comprising said monodisperse microspheres and said colloidal particles, to form a mixture and allow a reaction to occur wherein at least one of said first and second binding molecules binds said analyte, said reaction being formation or decomplexation of said immunocomplex, so that the reacted mixture includes microspheres in uncompleted form, in said immunocomplex, or both, wherein the degree of binding of said microspheres to the colloidal particles in the reacted mixture, or the degree of decomplexation of the immunocomplex, is dependent upon presence or amount of said analyte in said fluid sample;
   (b) illuminating the reacted mixture with an incident light source to produce individual light scatter signals for each of said microspheres;
   (c) measuring said light scatter signals;
   (d) determining a degree of variation of a statistical distribution of the measured light scatter signals from said microspheres, such that the degree of variation of said statistical distribution varies with the degree of binding of said microspheres with said colloidal particles in said reacted mixture; and
   (e) correlating said degree of variation of said statistical distribution of said light scatter signals for said microspheres in said reacted mixture with the presence or amount of said analyte in said fluid sample.

2. The method according to claim 1, wherein step (e) comprises correlating said degree of variation of said statistical distribution of said measurers light scatter signals with the amount of said analyte in said fluid sample.

3. The method according to claim 1, further comprising step of determining a statistical distribution of measured light scatter signals produced by a control.

4. The method according to claim 3, wherein said control comprises said first binding molecule-coated monodisperse microspheres.

5. The method according to claim 3, wherein said control comprises said immunocomplex.

6. The method according to claim 3, further comprising step (g) of normalizing the statistical distribution of said measured light scatter signals obtained in step (d) with respect to said control light scatter signal determination obtained in step (f).

7. The method according to claim 1, wherein said light scatter signals produced in said step (b) comprise low angle forward light scatter signals.

8. The method according to claim 1, wherein said light scatter signals produced in step (b) comprise forward light scatter signals from about 10° to about 80°.

9. The method according to claim 1, wherein said light scatter signals produced in step (b) comprise substantially right angle light scatter signals.

10. The method according to claim 1, wherein said light scatter signals produced in said step (b) comprise backscatter signals of from about 100° to about 170°.

11. The method according to claim 1, wherein said distribution is a distribution of amplitudes of the light scatter signals.

12. The method according to claim 11, wherein said distribution is a histogram of the amplitudes.

13. The method according to claim 1, wherein said distribution is a distribution of integrated areas of the light scatter signals.

14. The method according to claim 13, wherein said distribution is a histogram of the integrated areas.

15. The method according to claim 1, wherein said individual light scatter signals are produced for each of said microspheres by directing said incident light source onto each microsphere and monitoring light scattered therefrom and each individual light scatter signal is a ratio between an amplitude of light scattered at a low angle by the microsphere and an amplitude of light scattered at a high angle by the microsphere.

16. The method according to claim 1, wherein said distribution is a distribution of pulse width times maximum amplitude of the light scatter signals.

17. The method according to claim 16, wherein said distribution is a histogram of the pulse width times the maximum amplitude of the light scatter signals.

18. The method according to claim 1, wherein said illuminating is performed on a stream of the reacted mixture directed through an optical sheath flow particle analyzer comprising a sheath flow cell having a predetermined central bore diameter.

19. The method according to claim 18, wherein said predetermned central bore diameter is from about 100 µm to about 500 µm.

20. The method according to claim 19, wherein said predetermined central bore diameter is about 250 µm.

21. The method according to claim 18, wherein said stream has a substantially constant diameter.

22. The method according to claim 21, wherein said stream diameter is from about 3µ to about 10µ.

23. The method according to claim 1, wherein said incident light source is a laser light source.

24. The method according to claim 1, wherein said analyte is an antigen, antibody, hapten, nucleic acid or ligand.

25. The method according to claim 1, wherein said first binding molecule and said second binding molecule are complementary to said analyte.

26. The method according to claim 25, wherein said first binding molecule is an antibody specific to said analyte.

27. The method according to claim 25, wherein said second binding molecule is an antibody specific to said analyte.

28. The method according to claim 25, wherein said first binding molecule is a monoclonal antibody specific to said analyte.

29. The method according to claim 25, wherein said second binding molecule is a monoclonal antibody specific to said analyte.

30. The method according to claim 25, wherein said first binding molecule is a monoclonal antibody specific to a first epitope on said analyte, and said second binding molecule is a monoclonal antibody specific to a second epitope on said analyte.

31. The method according to claim 1, wherein said first binding molecule is said analyte.

32. The method according to claim 1, wherein said second binding molecule is complementary to said analyte.

33. The method according to claim 32, wherein said second binding molecule is an antibody specific to said analyte.

34. The method according to claim 33, wherein said antibody is a monoclonal antibody.

35. The method according to claim 1, wherein said monodisperse microspheres comprise a synthetic polymeric material.

36. The method according to claim 35, wherein said polymeric material comprises polybutadiene, polystyrene or a derivative thereof.

37. The method according to claim 1, wherein said monodisperse microspheres are glass microspheres.

38. The method according to claim 1, wherein said monodisperse microspheres comprise microscopic oxide powders.

39. The method according to claim 1, wherein said monodisperse microspheres have an average diameter of from about 0.25 µm to about 100 µm.

40. The method according to claim 39, wherein said average diameter is from about 0.25 µm to about 10 µm.

41. The method according to claim 39, wherein said average diameter is from about 0.5 µm to about 5.0 µm.

42. The method according to claim 1, wherein said colloidal particles are polydisperse.

43. The method according to claim 1, wherein said colloidal particles comprise a metal or a metal compound.

44. The method according to claim 43, wherein said metal compound is an oxide, hydroxide or a salt.

45. The method according to claim 43, wherein said metal is gold, platinum, silver or copper.

46. The method according to claim 45, wherein said metal is gold.

47. The method according to claim 1, wherein said colloidal particles have diameters ranging from about 20 nm to about 120 nm.

48. The method according to claim 47, wherein said diameters range from about 50 nm to about 80 nm.

49. The method according to claim 1, wherein said monodisperse microspheres have a first average diameter and said colloidal particles have a second average diameter, said first and second average diameters having a ratio of the average diameter of said monodisperse microspheres to the average diameter of said colloidal particles of from about 15:1 to about 30:1.

50. The method according to claim 1, wherein said colloidal particles and said monodisperse microspheres are present in said reagent set in a ratio effective to reduce interference by non-specific binding substances.

51. The method according to claim 50, wherein the ratio of said colloidal particles to said monodisperse microspheres is from about 2:1 to about 100,000:1.

52. The method according to claim 51 wherein said ratio is from about 1,000:1 to about 10,000:1.

53. The method according to claim 1, further comprising step (a') of separating the immunocomplex and the uncomplexed microspheres from the said reacted mixture prior to step (b) of illuminating and illuminating the immunocomplex separated from the reacted mixture in step (b) to produce said individual light scatter signals.

54. The method of claim 1, wherein diameters of said monodisperse microspheres have a coefficient of variation less than 5%.

55. The method of claim 1, wherein diameters of said monodisperse microspheres have a coefficient of variation of from about 1% to about 2%.

56. The method of claim 1, wherein diameters of said monodisperse microspheres have a coefficient of variation less than 2%.

57. A particle light scatter-based immunoassay for simultaneously measuring more than one analyte in a fluid sample, comprising steps:

(a) combining with said fluid sample for each said more than one analyte, a reagent set including first binding molecule-coated monodisperse microspheres and second binding molecule-coated colloidal particles smaller than said microspheres, or an immunocomplex comprising said monodisperse microspheres and said colloidal particles, to form a mixture of fluid sample and all reagent sets together and allow a reaction to occur wherein at least one of said first and second binding molecules of each said reagent set binds a respective one of said more than one analyte, said reaction being formation or decomplexation of each said immunocomplex, so that the reacted mixture includes microspheres of each said reagent set in uncomplexed form, in said immunocomplex, or both, wherein the degree of binding of said microspheres to the colloidal particles of each said reagent set in the reacted mixture, or the degree of decomplexation of each said immunocomplex, is dependent upon presence or amount of each said more than one analyte in said fluid sample;

(b) illuminating the reacted mixture with an incident light source to produce individual light scatter signals for each of said microspheres wherein the light scatter signals produced for the microspheres of each said reagent set are resolvable from the light scatter signals produced for the microspheres of any other said reagent set;

(c) measuring said light scatter signals;

(d) determining a degree of variation of a statistical distribution of the measured light scatter signals from said microspheres of each said reagent set, such that the degree of variation of said statistical distribution varies with the degree of binding of said microspheres with said colloidal particles of each said reagent set in said reacted mixture; and (e) correlating said degree of variation of eh said statistical distribution of said light scatter signals for said microspheres in said reacted mixture with the presence or amount of each respective one of said more than one analyte in said fluid sample.

* * * * *

UNITED STATES PATENT AND TRADEMARK OFFICE
CERTIFICATE OF CORRECTION

PATENT NO. : 6,200,820 B1
DATED : March 13, 2001
INVENTOR(S) : Hansen et al.

It is certified that error appears in the above-identified patent and that said Letters Patent is hereby corrected as shown below:

Title page, Item [57],
ABSTRACT, line 11, delete "microsphere".

Column 2,
Line 18, "aremet" should read -- are met --.

Column 3,
Line 9, after "complex" delete -- : --.

Column 6,
Line 4, after "is" delete -- , --.
Line 25, "at" should read -- a --.
Line 48, "f low" should read -- flow --.

Column 9,
Line 51, "tea" should read -- to --.

Column 14,
Line 46, "car" should read -- can --.

Column 16,
Line 10, "rangre" should read -- range --.

Column 17,
Line 5, after "configuration" insert -- , --
Line 7, after "NaN$_3$" insert -- and --.
Line 16, after "NaN$_3$" insert -- and --.
Line 24, "0.0%" should read -- 0.1% --.
Lines 61-62, "immunoconiplex" should read -- immunocomplex --.

UNITED STATES PATENT AND TRADEMARK OFFICE
CERTIFICATE OF CORRECTION

PATENT NO.   : 6,200,820 B1
DATED         : March 13, 2001
INVENTOR(S)  : Hansen et al.

It is certified that error appears in the above-identified patent and that said Letters Patent is hereby corrected as shown below:

<u>Column 18,</u>
Line 8, "eh" should read -- each --.
Line 23, "measurers" should read -- measured --.
Line 26, after "step" insert -- (f) --.

Signed and Sealed this

Sixteenth Day of October, 2001

Attest:

*Nicholas P. Godici*

NICHOLAS P. GODICI
*Attesting Officer*   *Acting Director of the United States Patent and Trademark Office*